US012599367B2

(12) United States Patent
Halmann et al.

(10) Patent No.: US 12,599,367 B2
(45) Date of Patent: Apr. 14, 2026

(54) METHODS AND SYSTEMS FOR GENERATING 3D PLEURAL SURFACES

(71) Applicant: GE Precision Healthcare LLC, Wauwatosa, WI (US)

(72) Inventors: Menachem Halmann, Wauwatosa, WI (US); Carmit Shiran, Middleton, WI (US); Radhika Madhavan, Niskayuna, NY (US); Alex Sokulin, Haifa (IL); Lev Greenberg, Haifa (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 250 days.

(21) Appl. No.: 18/331,049

(22) Filed: Jun. 7, 2023

(65) Prior Publication Data

US 2024/0407762 A1     Dec. 12, 2024

(51) Int. Cl.
| | |
|---|---|
| *A61B 8/00* | (2006.01) |
| *A61B 8/08* | (2006.01) |
| *A61B 8/14* | (2006.01) |
| *G16H 30/20* | (2018.01) |

(52) U.S. Cl.
CPC .............. *A61B 8/5207* (2013.01); *A61B 8/08* (2013.01); *A61B 8/145* (2013.01); *A61B 8/4483* (2013.01); *A61B 8/466* (2013.01); *A61B 8/5269* (2013.01); *G16H 30/20* (2018.01)

(58) Field of Classification Search
CPC ...... A61B 8/5207; A61B 8/145; A61B 8/4483
See application file for complete search history.

(56) References Cited

U.S. PATENT DOCUMENTS

| | | | |
|---|---|---|---|
| 10,667,793 B2 | 6/2020 | Halmann et al. | |
| 10,758,206 B2 | 9/2020 | Halmann et al. | |
| 11,227,392 B2 | 1/2022 | Halmann | |
| 2005/0135707 A1 * | 6/2005 | Turek | G06T 7/38 |
| | | | 382/128 |
| 2019/0336108 A1 * | 11/2019 | Hope Simpson | A61B 8/5207 |
| 2022/0061813 A1 * | 3/2022 | Halmann | A61B 8/5253 |
| 2023/0316642 A1 * | 10/2023 | Mory | G06T 15/08 |
| | | | 345/418 |

FOREIGN PATENT DOCUMENTS

| | | | | |
|---|---|---|---|---|
| WO | WO-2016112383 A1 * | 7/2016 | | G09B 19/00 |

OTHER PUBLICATIONS

Wotjczak, J. et al., "High-frequency ultrasound in ex vivo animal lungs in pulmonary edema," Journal of Anesthesiology & Clinical Science, vol. 2, No. 1, Jan. 2013, 5 pages.

* cited by examiner

*Primary Examiner* — Rochelle D Turchen
(74) *Attorney, Agent, or Firm* — McCoy Russell LLP

(57) ABSTRACT

Various methods and systems are provided for a medical imaging system. In one embodiment, a method includes generating a three-dimensional (3D) pleural surface viewed from an inside of the lung and looking outward based on ultrasound imaging signals. The 3D pleural surface may be generated from 2D or 3D ultrasound images. The method further comprises shading the generated 3D pleural surface via at least one virtual light source positioned as if inside the lung.

16 Claims, 13 Drawing Sheets

METHODS AND SYSTEMS FOR GENERATING 3D PLEURAL SURFACES

FIELD

Embodiments of the subject matter disclosed herein relate to ultrasound imaging and, in particular, to visualizing a lung pleura as a three-dimensional (3D) surface viewed from an inside of a lung and looking outward.

BACKGROUND

An ultrasound imaging system typically includes an ultrasound probe that is applied to a patient's body and a workstation or device that is operably coupled to the probe. During a scan, the probe may be controlled by an operator of the system and is configured to transmit and receive ultrasound signals that are processed into an ultrasound image by the workstation or device. The workstation or device may show the ultrasound images as well as a plurality of user-selectable inputs through a display device. The operator or other user may interact with the workstation or device to analyze the images displayed on and/or selected from the plurality of user-selectable inputs.

As one example, ultrasound imaging may be used for examining a patient's lungs due to an ease of use of the ultrasound imaging system at a point-of-care and resource availability relative to a chest x-ray or a chest computed tomography (CT) scan, for example. Further, the ultrasound imaging system does not expose the patient to radiation. Lung ultrasound imaging, also termed lung sonography, includes interpreting topography of a lung pleura for diagnostic purposes.

BRIEF DESCRIPTION

This summary introduces concepts that are described in more detail in the detailed description. It should not be used to identify essential features of the claimed subject matter, nor to limit the scope of the claimed subject matter.

In one aspect, a method for imaging a lung of a patient includes generating a three-dimensional (3D) pleural surface viewed from an inside of the lung and looking outward, based on ultrasound imaging signals. The 3D pleural surface may be generated from 2D or 3D ultrasound images. The method further comprises shading the generated 3D pleural surface via at least one virtual light source positioned as if inside the lung.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Embodiments of the present disclosure will now be described, by way of example, with reference to the FIGS. 1-13, which relate to various embodiments for generating a 3D representation of a pleural surface of a lung pleura viewed from an inside of a lung and looking outward. It is to be understood that, as described herein, a "3D pleural surface" is a 3D computer rendering which represents an anatomical region (e.g., a pleura) captured using an imaging system. In an aerated lung, the pleura, which form the outer boundary of the lung that lies against the chest wall, may provide the substantially only anatomical lung structure detectable by ultrasound. The pleura appear as a hyperechoic horizontal segment of brighter (e.g., whiter) pixels in a 2D ultrasound image, referred to as a pleural line, which moves synchronously with respiration in a phenomenon known as pleural sliding. The 3D pleural surface includes a volumetric topography of the lung pleura. Some topography of the pleura is shown in 2D ultrasound images, however further detail of pleura topography may be visualized in a 3D pleural surface, which may help in identifying and/or diagnosing conditions of the lung that may be visualized as irregularities in pleural surface topography. Compared to what may be captured in a 2D ultrasound image, the 3D pleural surface may show pleural topography in a broader region of the lung. For example, the 3D pleural surface may be a live 3D surface rendering of the pleura, or may be a static image provided following data collection using the ultrasound probe. In some embodiments, the 3D pleural surface described herein may be a 4D image, where the 3D pleural surface is a 3D image which may change over time (e.g., in real-time) to reflect changes in patient anatomy visualized using the ultrasound probe (e.g., due to patient breathing, movement, etc.).

Figure 1:
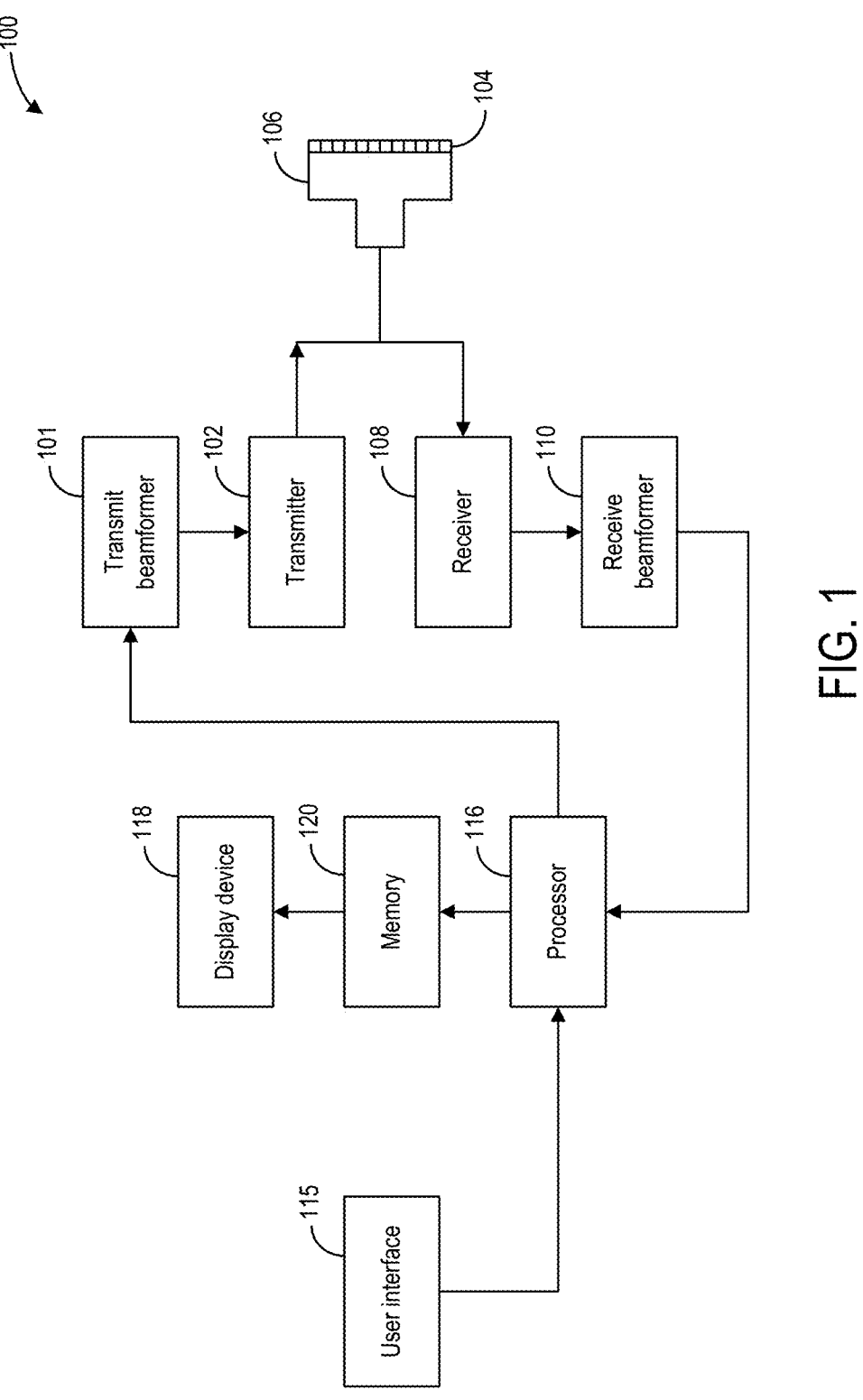
FIG. 1 shows a block schematic diagram of an ultrasound imaging system, according to an embodiment.
Figure 2:
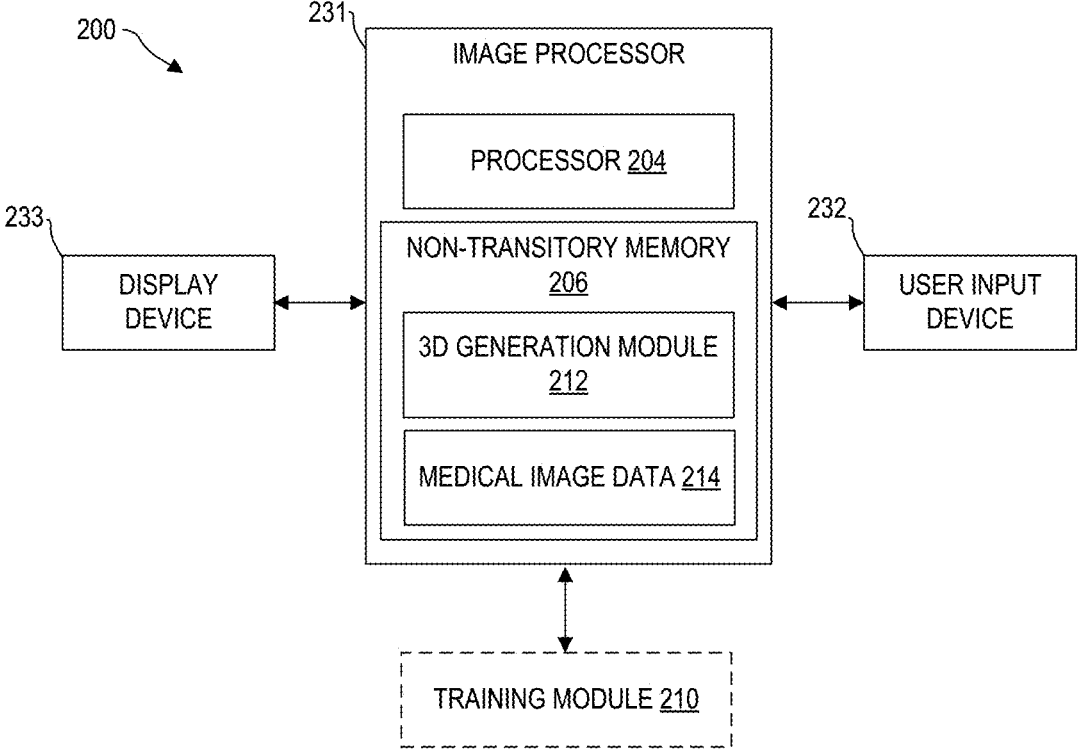
FIG. 2 is a schematic diagram illustrating an image processing system for generating 3D pleural surfaces, according to embodiment.
Figure 8:
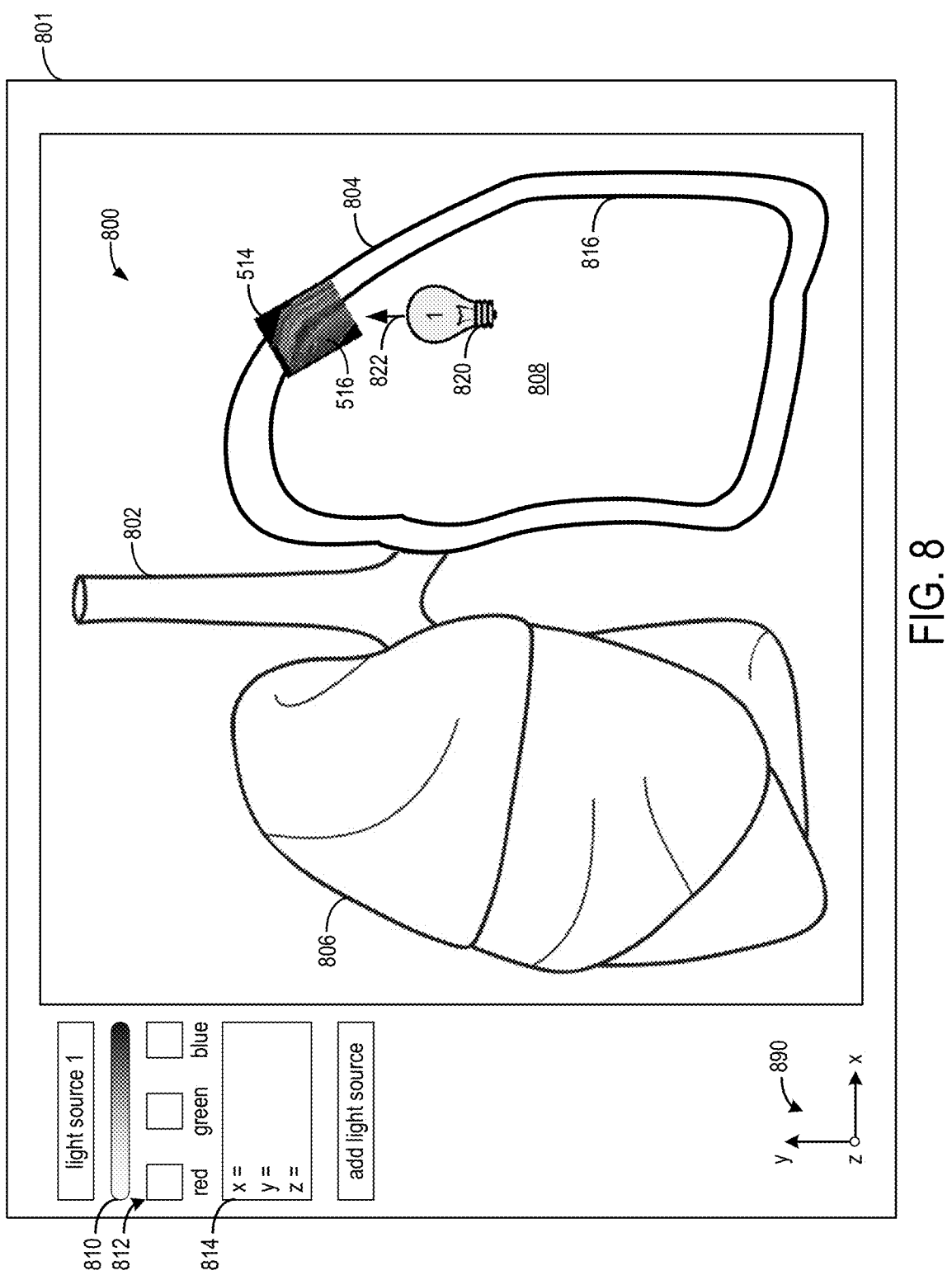
FIG. 8 shows a first example display including a 3D pleural surface, according to an embodiment.
Figure 9:
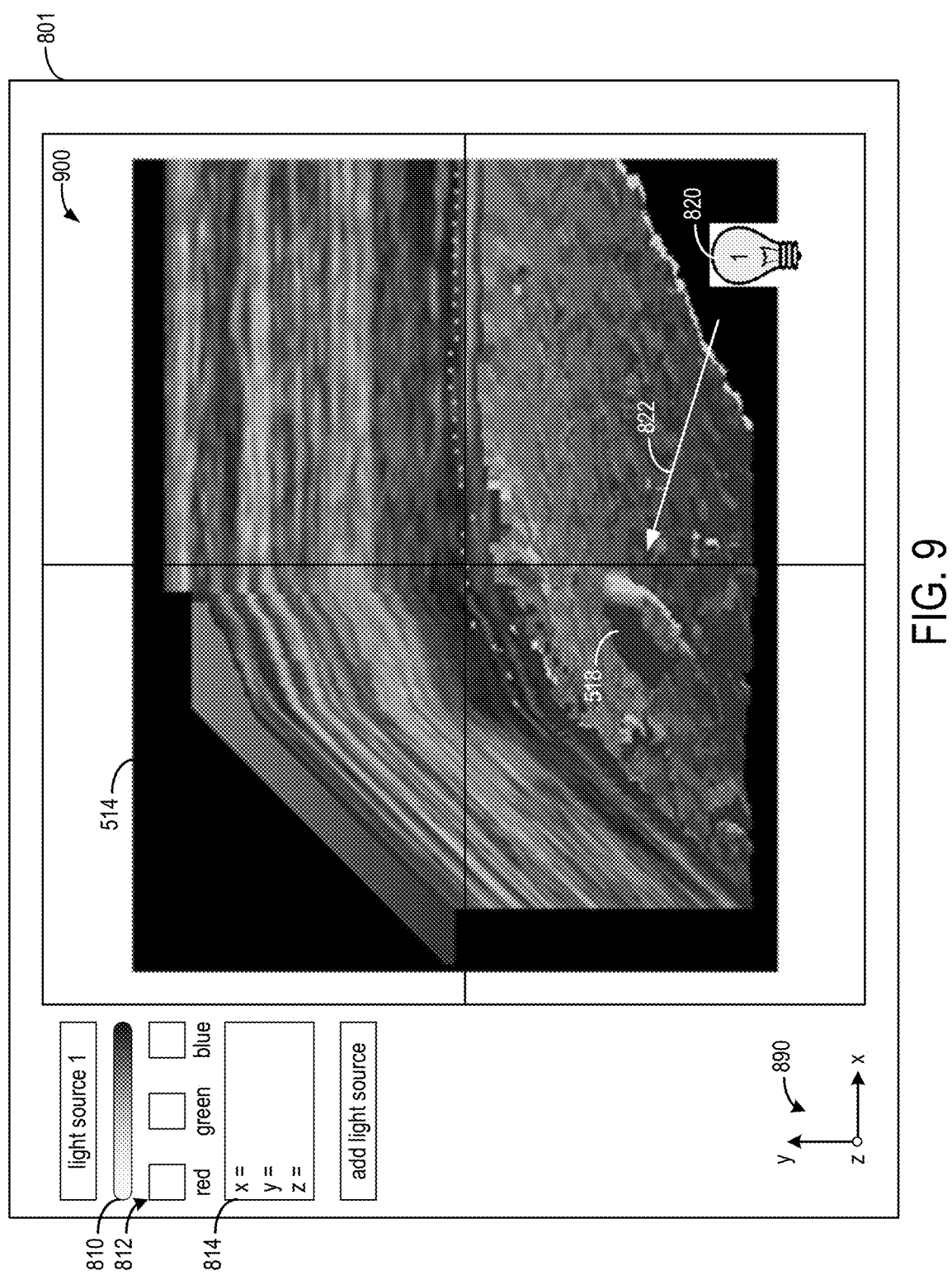
FIG. 9 shows a second example display including a 3D pleural surface, according to an embodiment.
Figure 10:
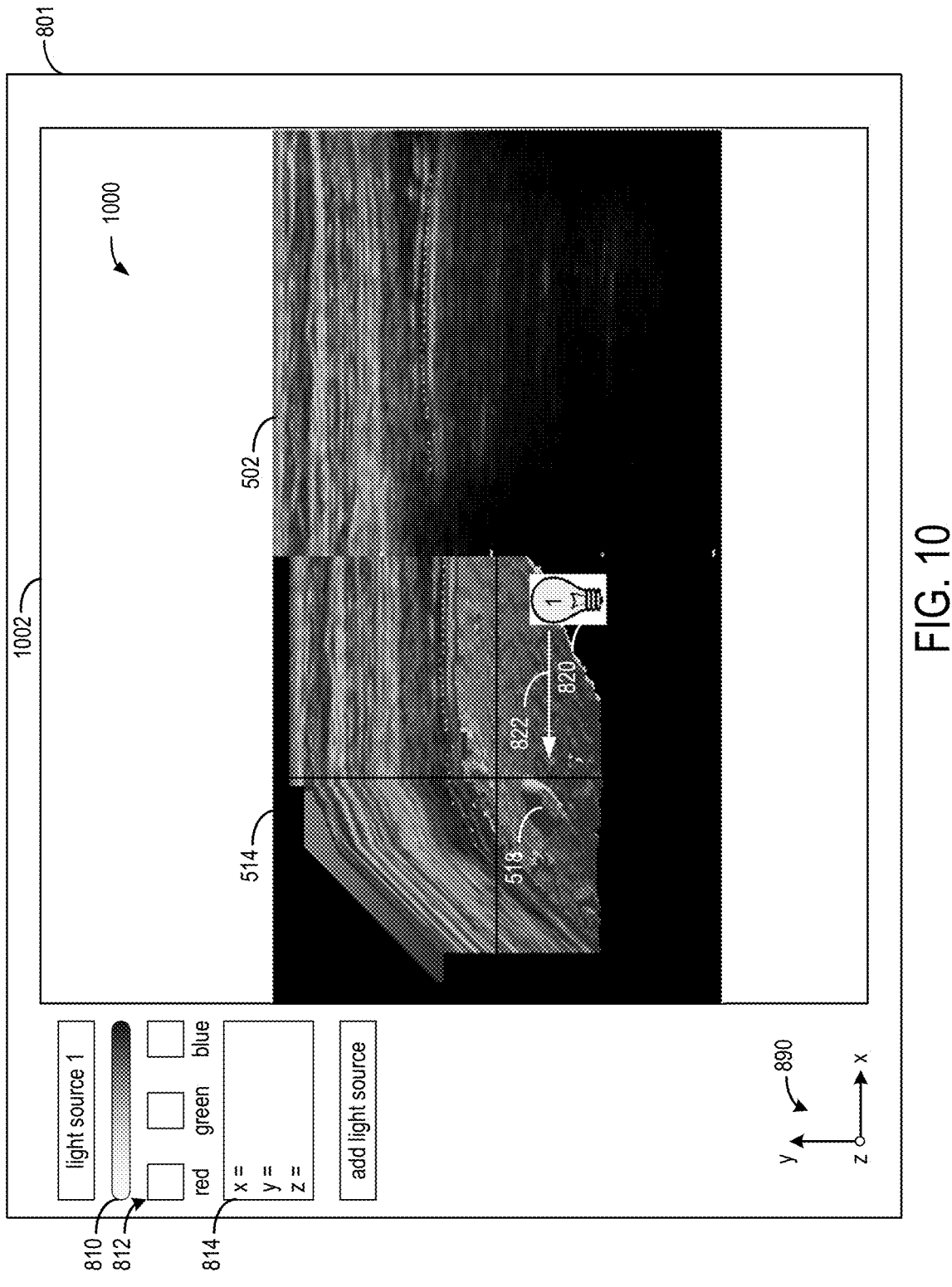
FIG. 10 shows a third example display including a 3D pleural surface, according to an embodiment.
Figure 12:
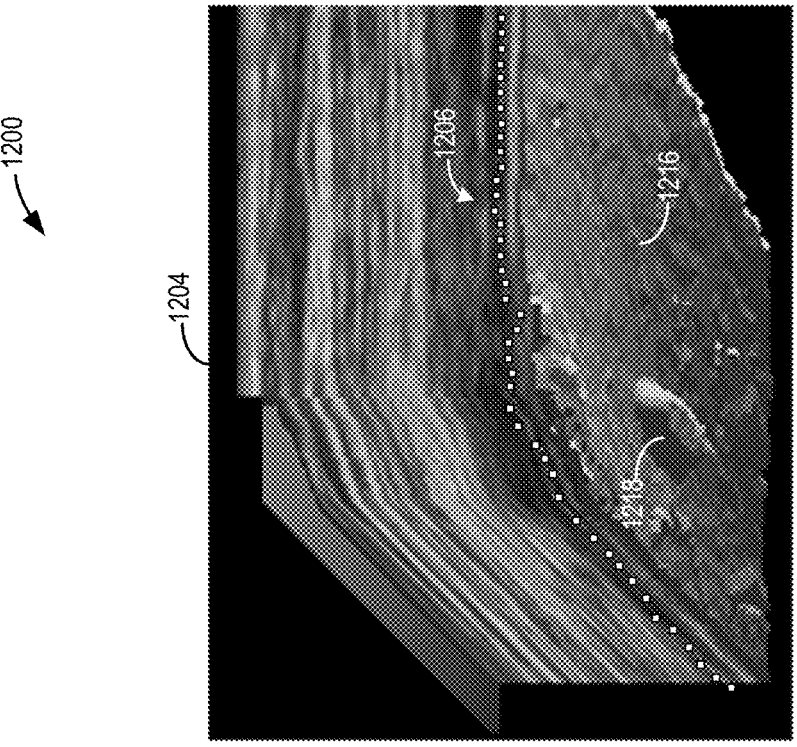
FIG. 12 shows an example set of images generated according to the method of FIG. 11.
Figure 12:
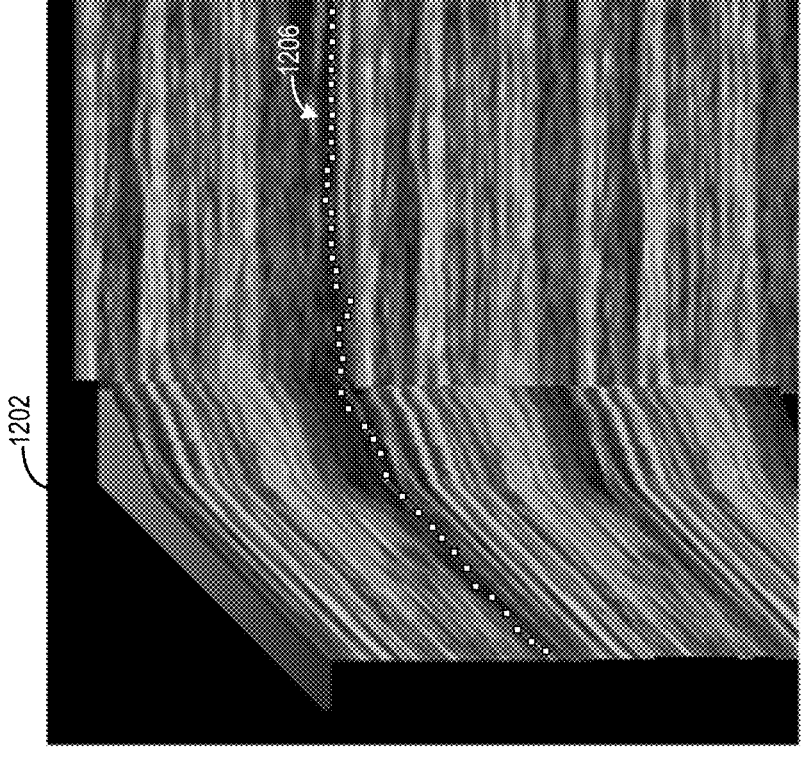
Figure 13:
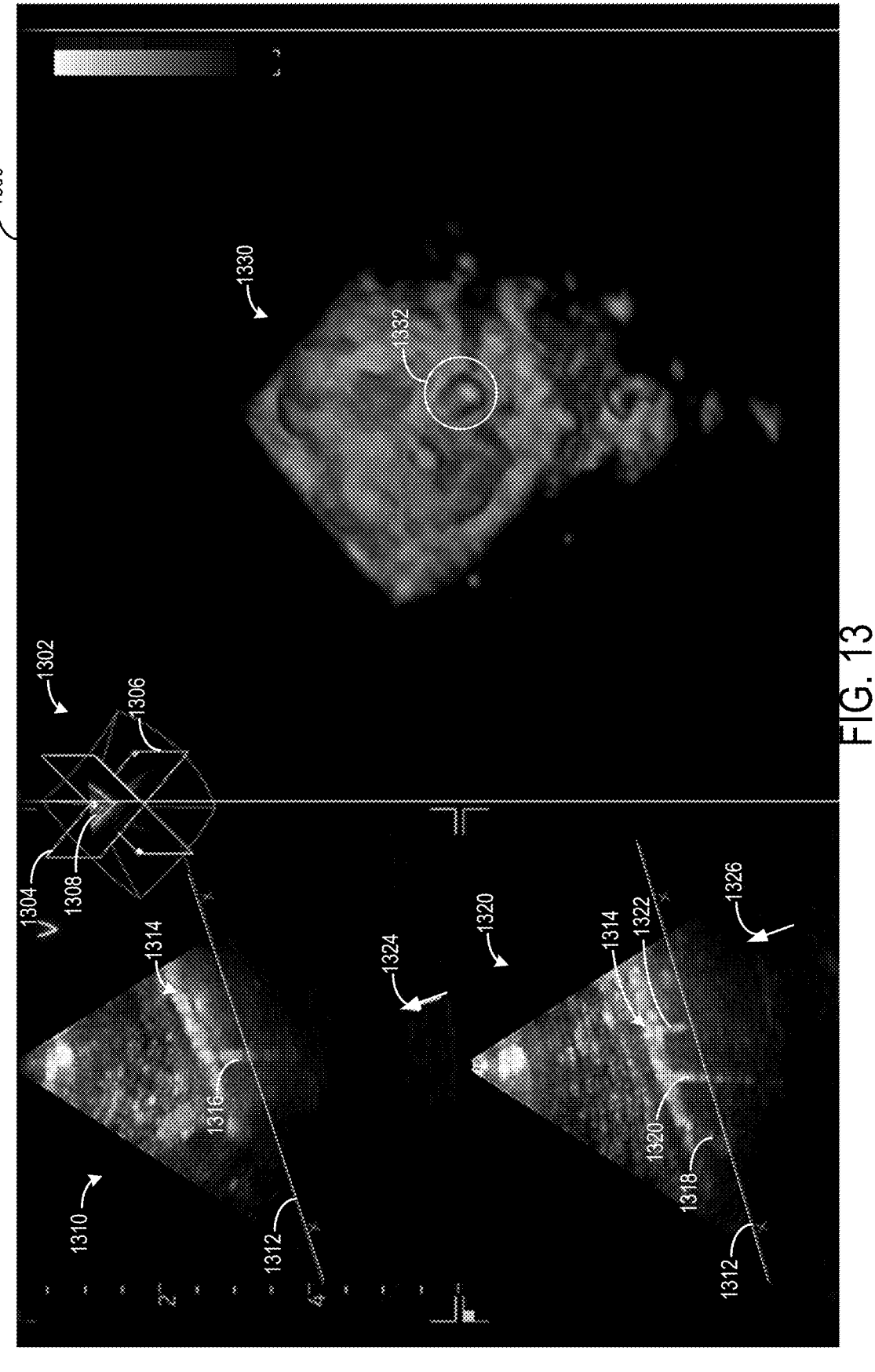
FIG. 13 shows a fourth example display including biplane and 3D displays of a lung.

The 3D pleural surface may be generated based on medical imaging data acquired by an imaging system, such as the ultrasound imaging system shown in FIG. 1. As the processes described herein may be applied to pre-processed imaging data and/or to processed images, the term "image" is generally used throughout the disclosure to denote both pre-processed and partially-processed image data (e.g., pre-beamformed RF or I/Q data, pre-scan converted RF data) as well as fully processed images (e.g., scan converted and filtered images ready for display). An example image processing system that may be used to generate the 3D pleural surface is shown in FIG. 2. The image processing system may employ image processing techniques and one or more algorithms to identify a pleural line in ultrasound imaging data and generate a 3D pleural surface viewed from an inside of a lung and looking outward. The 3D pleural surface may be generated from 2D ultrasound images, as described with respect to the method of FIG. 3. Various visual markers or indicators may be used to identify the pleural line in a 2D ultrasound image, such as illustrated in FIG. 4. In some embodiments, generating the 3D pleural surface includes stacking multiple 2D ultrasound images of a same lung in which the pleural line has been identified, as described with respect to FIG. 5. In some embodiments, the 3D pleural surface is generated from a mesh which is based on a series of 2D ultrasound images, as described with respect to FIG. 6. In some embodiments, the 3D pleural surface is generated from a 3D volumetric image, as described with respect to the method of FIG. 11. FIG. 12 shows example 3D ultrasound images generated according to the method of FIG. 11. Following generation of the 3D pleural surface, shading may be applied to highlight irregularities of the 3D pleural surface, as described with respect to the method of FIG. 7. FIGS. 8-10 show example displays including the 3D pleural surface viewed from an inside of a lung and looking outward. FIG. 13 shows biplane and 3D images of a lung. In this way, pleural irregularities may be highlighted in a display of a 3D pleural surface generated from volumetric ultrasound imaging data in real-time, decreasing a time until a diagnosis can be made and decreasing both intra-operator and inter-operator variation.

Advantages that may be realized in the practice of some embodiments of the described systems and techniques are that inconsistencies in the detection of pleural irregularities, particularly between different operators, may be decreased. This may be particularly advantageous for increasing a detection accuracy of point-of-care ultrasound operators, who may have less training than ultrasound experts (e.g., sonographers or radiologists). For example, an emergency room physician, who may not receive expert-level ultrasound training, may be more likely to overlook an irregularity or incorrectly identify a normal structure or an imaging artifact as an irregularity, which may increase a burden on a radiology department for follow up scans and increase patient discomfort. Further, by decreasing follow up scans and a mental burden on the point-of-care ultrasound operator, an amount of time until an accurate diagnosis is made may be decreased. Although the systems and methods described below for evaluating medical images are discussed with reference to an ultrasound imaging system, it may be noted that the methods described herein may be applied to a plurality of imaging systems (e.g., MRI, PET, x-ray, CT, or other similar systems).

Referring to FIG. 1, a schematic diagram of an ultrasound imaging system 100 in accordance with an embodiment of the disclosure is shown. However, it may be understood that embodiments set forth herein may be implemented using other types of medical imaging modalities (e.g., magnetic resonance imaging, computed tomography, positron emission tomography, and so on). The ultrasound imaging system 100 includes a transmit beamformer 101 and a transmitter 102 that drives transducer elements 104 within a transducer array, herein referred to as a probe 106, to emit pulsed ultrasonic signals (referred to herein as transmit pulses) into a body (not shown). According to an embodiment, the probe 106 may be a one-dimensional (1D) transducer array probe. In some embodiments, the probe 106 may be a two-dimensional (2D) matrix transducer array probe. In further embodiments, the probe 106 may be a 1.5-dimensional (1.5D) probe or any ultrasound probe capable of live 3D imaging, such as a matrix array probe. The transducer elements 104 may be comprised of a piezoelectric material. When a voltage is applied to the piezoelectric material, the piezoelectric material physically expands and contracts, emitting an ultrasonic spherical wave. In this way, the transducer elements 104 may convert electronic transmit signals into acoustic transmit beams.

After the transducer elements 104 of the probe 106 emit pulsed ultrasonic signals into a body (of a patient), the pulsed ultrasonic signals are back-scattered from structures within an interior of the body, like blood cells or muscular tissue, to produce echoes that return to the transducer elements 104. The echoes are converted into electrical signals, or ultrasound data, by the transducer elements 104, and the electrical signals are received by a receiver 108. The electrical signals representing the received echoes are passed through a receive beamformer 110 that performs beamforming and outputs ultrasound data, which may be in the form of a radiofrequency (RF) signal. Additionally, the transducer elements 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be positioned within the probe 106. The terms "scan" or "scanning" may also be used in this disclosure to refer to acquiring data through the process of transmitting and receiving ultrasonic signals. The term "data" may be used in this disclosure to refer to one or more datasets acquired with an ultrasound imaging system.

A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of a rotary element, a mouse, a keyboard, a trackball, hard keys linked to specific actions, soft keys that may be configured to control different functions, and a graphical user interface displayed on a display device 118. In some embodiments, the display device 118 may include a touch-sensitive display, and thus, the display device 118 may be included in the user interface 115.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. As used herein, the term "electronic communication" may be defined to include both wired and wireless communications. The processor 116 may control the probe 106 to acquire data according to instructions stored on a memory of the processor and/or a memory 120. As one example, the processor 116 controls which of the transducer elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processing unit (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates RF data and generates raw data. In another embodiment, the demodulation can be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay (e.g., substantially at the time of occurrence). For example, an embodiment may acquire images at a real-time rate of 7-20 frames/sec. The ultrasound imaging system 100 may acquire two-dimensional (2D) data of one or more planes at a significantly faster rate. However, it should be understood that the real-time frame-rate may be dependent on a length (e.g., duration) of time that it takes to acquire and/or process each frame of data for display. Accordingly, when acquiring a relatively large amount of data, the real-time frame-rate may be slower. For example, the ultrasound imaging system 100 may additionally or alternatively acquire three-dimensional (3D) data. Thus, some embodiments may have real-time frame-rates that are considerably faster than 20 frames/sec while other embodiments may have real-time frame-rates slower than 7 frames/sec.

In some embodiments, the data may be stored temporarily in a buffer (not shown) during a scanning session and processed in less than real-time in a live or off-line (e.g., freeze) operation. Some embodiments of the disclosure may include multiple processors (not shown) to handle the processing tasks that are handled by the processor 116 according to the exemplary embodiment described hereinabove. For example, a first processor may be utilized to demodulate and decimate the RF signal while a second processor may be used to further process the data, for example, by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on the display device 118. Other embodiments may acquire and display data at different rates. For example, some embodiments may acquire data at a frame-rate of less than 10 Hz or greater than 30 Hz depending on the size of the frame and the intended application. The memory 120 may store processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 to form 2D or 3D images. When multiple images are obtained, the processor 116 may also be configured to stabilize or register the images. For example, one or more modules may generate B-mode, color Doppler, M-mode, color M-mode, color flow imaging, spectral Doppler, elastography, tissue velocity imaging (TVI), strain, strain rate, and the like, and combinations thereof. As one example, the one or more modules may process color Doppler data, which may include traditional color flow Doppler, power Doppler, high-definition (HD) flow Doppler, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real-time while a procedure (e.g., ultrasound imaging) is being performed on a patient. The video processor module may include a separate image memory, and the ultrasound images may be written to the image memory in order to be read and displayed by the display device 118.

Further, the components of the ultrasound imaging system 100 may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as the probe 106 and the user interface 115. Optionally, the ultrasound imaging system 100 may be a unitary system that is capable of being moved (e.g., portably) from room to room. For example, the ultrasound imaging system 100 may include wheels or may be transported on a cart, or may comprise a handheld device.

For example, in various embodiments of the present disclosure, one or more components of the ultrasound imaging system 100 may be included in a portable, handheld ultrasound imaging device. For example, the display device 118 and the user interface 115 may be integrated into an exterior surface of the handheld ultrasound imaging device, which may further contain the processor 116 and the memory 120 therein. The probe 106 may comprise a handheld probe in electronic communication with the handheld ultrasound imaging device to collect raw ultrasound data. The transmit beamformer 101, the transmitter 102, the receiver 108, and the receive beamformer 110 may be included in the same or different portions of the ultrasound imaging system 100. For example, the transmit beamformer 101, the transmitter 102, the receiver 108, and the receive beamformer 110 may be included in the handheld ultrasound imaging device, the probe, and combinations thereof.

Referring to FIG. 2, an example medical image processing system 200 is shown. In some embodiments, the medical image processing system 200 is incorporated into a medical imaging system, such as an ultrasound imaging system (e.g., the ultrasound imaging system 100 of FIG. 1), an MRI system, a CT system, a single-photon emission computed tomography (SPECT) system, etc. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processor 231, a user input device 232, and a display device 233. For example, the image processor 231 may be operatively/communicatively coupled to the user input device 232 and the display device 233.

The image processor 231 includes a processor 204 configured to execute machine-readable instructions stored in non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. In some embodiments, the processor 204 may include other electronic components capable of carrying out processing functions, such as a digital signal processor, a field-programmable gate array (FPGA), or a graphics board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

In the embodiment shown in FIG. 2, the non-transitory memory 206 stores a 3D generation module 212 and medical image data 214. The 3D generation module 212 includes one or more algorithms to process input medical images from the medical image data 214. Specifically, the 3D generation module 212 may generate a 3D pleural surface from 2D and/or 3D ultrasound images, as described with respect to FIGS. 3 and 11 respectively. For example, the 3D generation module 212 may include one or more image recognition algorithms, shape or edge detection algorithms, gradient algorithms, and the like to process input medical images. Additionally or alternatively, the 3D generation module 212 may store instructions for implementing a neural network, such as a convolutional neural network, for detecting pleural surfaces/pleura captured in the medical image data 214 in real-time. For example, the 3D generation module 212 may include trained and/or untrained neural networks and may further include training routines, or parameters (e.g., weights and biases), associated with one or more neural network models stored therein. In some embodiments, the 3D generation module 212 may evaluate the medical image data 214 as it is acquired in real-time. Additionally or alternatively, the 3D generation module 212 may evaluate the medical image data 214 offline, not in real-time.

As an example, when the medical image data 214 includes lung ultrasound data, the identified anatomical feature may include lung pleura, which may be identified by the 3D generation module 212 based on pleural sliding via edge detection techniques and/or gradient changes. As will be elaborated with respect to FIGS. 3 and 11, detection of pleural positioning may assist in indicating a region of an ultrasound image which is noise and may be removed to expose a pleural surface.

Optionally, the image processor 231 may be communicatively coupled to a training module 210, which includes instructions for training one or more of the machine learning models stored in the 3D generation module 212. The training module 210 may include instructions that, when executed by a processor, cause the processor to build a model (e.g., a mathematical model) based on sample data to make predictions or decisions regarding the detection and classification of anatomical irregularities without the explicit programming of a conventional algorithm that does not utilize machine learning. In one example, the training module 210 includes instructions for receiving training data sets from the medical image data 214. The training data sets comprise sets of medical images, associated ground truth labels/images, and associated model outputs for use in training one or more of the machine learning models stored in the 3D generation module 212. The training module 210 may receive medical images, associated ground truth labels/images, and associated model outputs for use in training the one or more machine learning models from sources other than the medical image data 214, such as other image processing systems, the cloud, etc. In some embodiments, one or more aspects of the training module 210 may include remotely-accessible networked storage devices configured in a cloud computing configuration. Further, in some embodiments, the training module 210 is included in the non-transitory memory 206. Additionally or alternatively, in some embodiments, the training module 210 may be used to generate the 3D generation module 212 offline and remote from the image processing system 200. In such embodiments, the training module 210 may not be included in the image processing system 200 but may generate data stored in the image processing system 200. For example, the 3D generation module 212 may be pre-trained with the training module 210 at a place of manufacture.

The non-transitory memory 206 further stores the medical image data 214. The medical image data 214 includes, for example, functional and/or anatomical images captured by an imaging modality, such as an ultrasound imaging system, an MRI system, a CT system, a PET system, etc. As one example, the medical image data 214 may include ultrasound images, such as lung ultrasound images. Further, the medical image data 214 may include one or more of 2D images, 3D images, static single frame images, and multi-frame cine-loops (e.g., movies).

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration. As one example, the non-transitory memory 206 may be part of a picture archiving and communication system (PACS) that is configured to store patient medical histories, imaging data, test results, diagnosis information, management information, and/or scheduling information, for example.

The image processing system 200 may further include the user input device 232. The user input device 232 may comprise one or more of a touchscreen, a keyboard, a mouse, a trackpad, a motion sensing camera, or other device configured to enable a user to interact with and manipulate data stored within the image processor 231.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206. In some embodiments, the display device 233 may be included in a smartphone, a tablet, a smartwatch, or the like.

It may be understood that the medical image processing system 200 shown in FIG. 2 is one non-limiting embodiment of an image processing system, and other imaging processing systems may include more, fewer, or different components without departing from the scope of this disclosure. Further, in some embodiments, at least portions of the medical image processing system 200 may be included in the ultrasound imaging system 100 of FIG. 1, or vice versa (e.g., at least portions of the ultrasound imaging system 100 may be included in the medical image processing system 200).

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3:
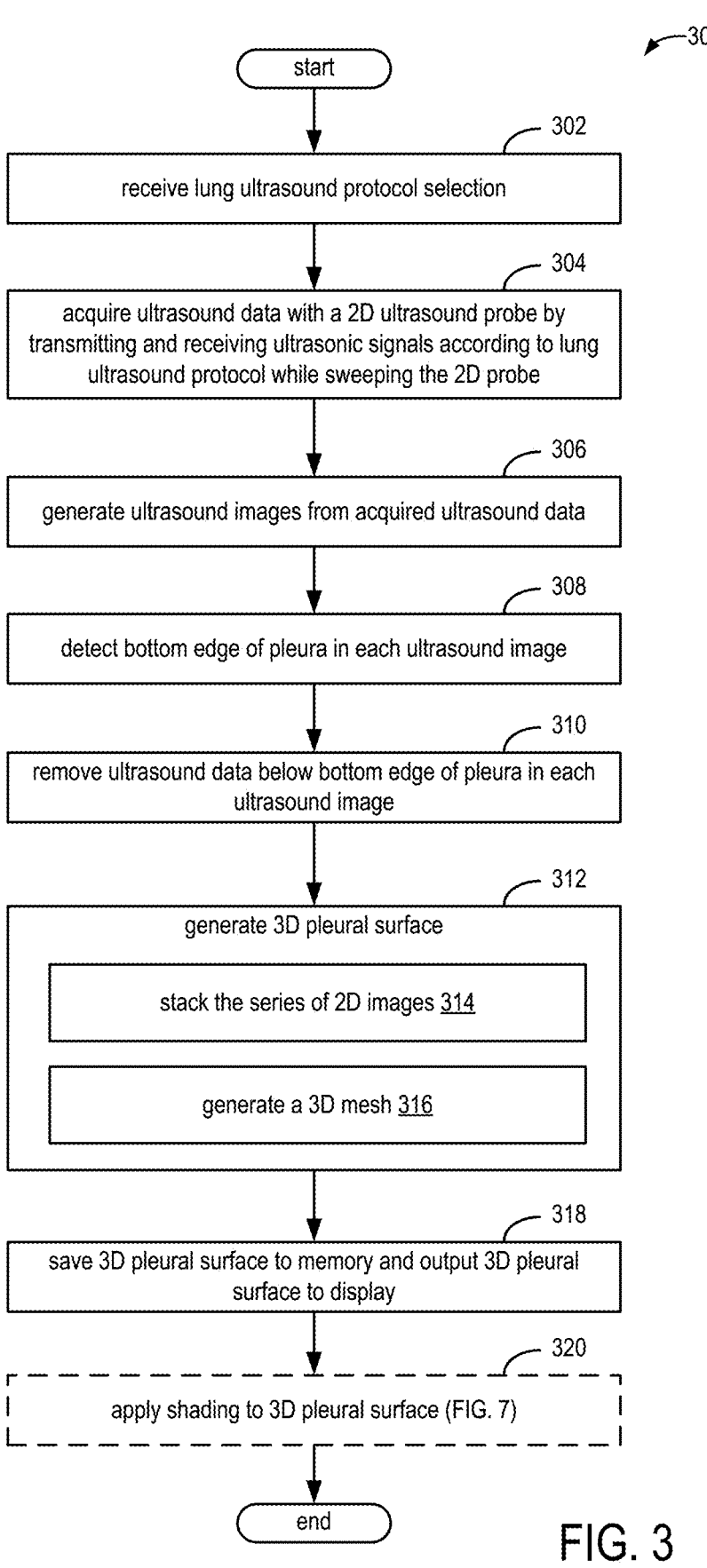
FIG. 3 shows a flowchart illustrating an example method for generating 3D pleural surfaces from 2D ultrasound images, according to an embodiment.
Figure 4:
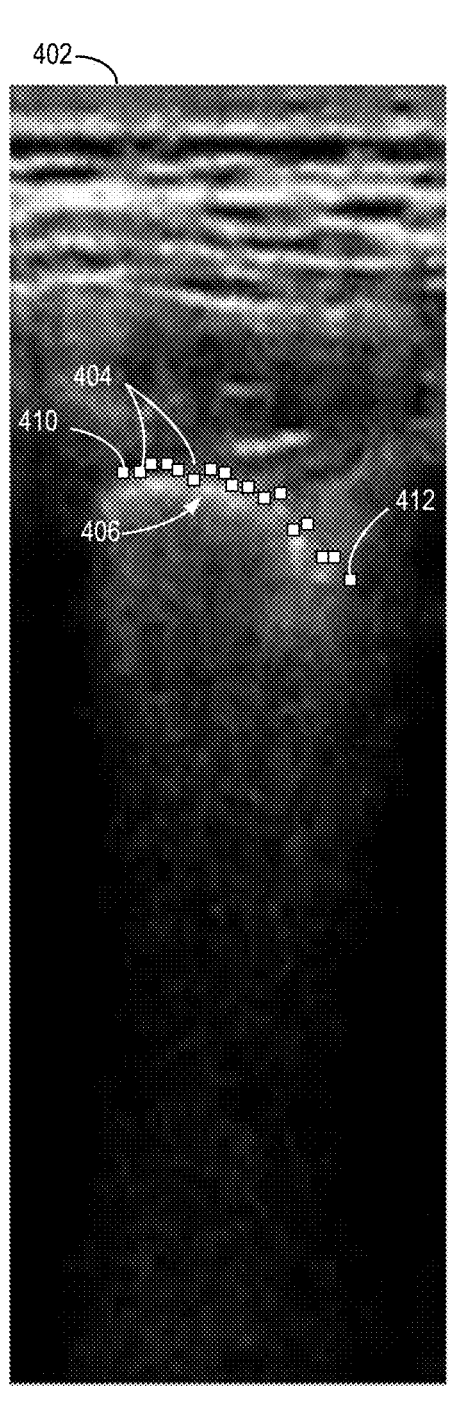
FIG. 4 shows a first example annotated 2D lung ultrasound image that may be used to generate a 3D pleural surface, according to an embodiment.

FIG. 3 shows a flow chart of an example method 300 for generating a 3D pleural surface, where ultrasound imaging signals used to generate the 3D pleural surface are acquired from positioning a 2D probe to acquire volumetric ultrasound data. The 3D pleural surface is viewed from an inside of a lung and looking outward. In particular, method 300 provides a workflow for generating the 3D pleural surface from a series of 2D images captured using the 2D probe by processing the series of 2D images to generate a stack of 2D images, and/or by generating a 3D mesh from the series of 2D images, from which a 3D image may be generated. Method 300 will be described for 2D ultrasound images acquired using an ultrasound imaging system, such as ultrasound imaging system 100 of FIG. 1, although other ultrasound imaging systems may be used. Further, method 300 may be adapted to other imaging modalities. Method 300 may be implemented by one or more of the above described systems, including the ultrasound imaging system 100 of FIG. 1 and medical image processing system 200 of FIG. 2. As such, method 300 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. Further, in some embodiments, method 300 is performed in real-time, as the 2D images are acquired, while in other embodiments, at least portions of method 300 are performed offline, after the 2D images are acquired. For example, the processor may evaluate 2D images that are stored in memory even while the ultrasound system is not actively being operated to acquire images (e.g., when data acquisition is frozen). Further still, at least parts of method 300 may be performed in parallel. For example, ultrasound data for a second 2D image may be acquired while a first 2D image is generated, ultrasound data for a third 2D image may be acquired while the first 2D image is analyzed, and so on.

At 302, method 300 includes receiving a lung ultrasound protocol selection. The lung ultrasound protocol may be selected by an operator (e.g., user) of the ultrasound imaging system via a user interface (e.g., the user interface 115). As one example, the operator may select the lung ultrasound protocol from a plurality of possible ultrasound protocols using a drop-down menu or by selecting a virtual button. Alternatively, the system may automatically select the protocol based on data received from an electronic health record (EHR) associated with the patient. For example, the EHR may include previously performed exams, diagnoses, and current treatments, which may be used to select the lung ultrasound protocol. Further, in some examples, the operator may manually input and/or update parameters to use for the lung ultrasound protocol. The lung ultrasound protocol may be a system guided protocol, where the system guides the operator through the protocol step-by-step, or a user guided protocol, where the operator follows a lab-defined or self-defined protocol without the system enforcing a specific protocol or having prior knowledge of the protocol steps.

Further, the lung ultrasound protocol may include a plurality of scanning sites (e.g., views), probe movements, and/or imaging modes that are sequentially performed. For example, the lung ultrasound protocol may include using real-time B-mode imaging with a convex, curvilinear, or linear ultrasound probe (e.g., the probe 106 of FIG. 1) configured to capture 2D ultrasound images. In some examples, the lung ultrasound protocol may further include using dynamic M-mode. The lung ultrasound protocol may include a longitudinal scan, wherein the probe is positioned perpendicular to the ribs, and/or an oblique scan, wherein the probe is positioned along intercostal spaces between ribs. Further still, in some examples, the lung ultrasound protocol may include a panoramic sweep, where the user sweeps the ultrasound probe from the head downward, and multiple views from the sweep may be stitched together to provide anatomical and spatial relationships.

At 304, method 300 includes acquiring ultrasound data with the ultrasound probe by transmitting and receiving ultrasonic signals according to the lung ultrasound protocol. Acquiring ultrasound data according to the lung ultrasound protocol may include the system displaying instructions on the user interface, for example, to guide the operator through the acquisition of the designated scanning sites. Additionally or alternatively, the lung ultrasound protocol may include instructions for the ultrasound system to automatically acquire some or all of the data or perform other functions. For example, the lung ultrasound protocol may include instructions for the user to move, rotate, tilt, and/or sweep the ultrasound probe, as well as to automatically initiate and/or terminate a scanning process and/or adjust imaging parameters of the ultrasound probe, such as ultrasound signal transmission parameters, ultrasound signal receive parameters, ultrasound signal processing parameters, or ultrasound signal display parameters. Further, the acquired ultrasound data include one or more image parameters calculated for each pixel or group of pixels (for example, a group of pixels assigned the same parameter value) to be displayed, where the one or more calculated image parameters include, for example, one or more of an intensity, velocity, color flow velocity, texture, graininess, contractility, deformation, and rate of deformation value.

At 306, method 300 includes generating ultrasound images from the acquired ultrasound data. For example, the signal data acquired during the method at 304 is processed and analyzed by the processor in order to produce a 2D ultrasound image at a designated frame rate. The processor may include an image processing module that receives the signal data (e.g., image data) acquired at 304 and processes the received image data. For example, the image processing module may process the ultrasound signals to generate slices or frames of ultrasound information (e.g., 2D ultrasound images) for displaying to the operator. In one example, generating the 2D image may include determining an intensity value for each pixel to be displayed based on the received image data. The 2D ultrasound images will also be referred to herein as "frames" or "image frames."

At 308, method 300 includes detecting a bottom edge of the pleura in each 2D ultrasound image. The pleura appear as a hyperechoic horizontal segment of brighter (e.g., whiter) pixels in the 2D ultrasound image, referred to as a pleural line, which moves synchronously with respiration in a phenomenon known as pleural sliding. Detecting the bottom edge of the pleura may include identifying lower and upper borders of the pleura based on a brightness change between pixels, such as by using edge detection techniques or gradient changes. For example, the processor may apply an edge detection algorithm, such as included in the 3D generation module 212 of FIG. 2, that comprises one or more mathematical methods for identifying points (e.g., pixels) at which the image brightness changes sharply and/or has discontinuities to identify the lower and upper borders of the pleural line. As one example, the processor may apply the edge detection algorithm to the area having the highest amount of local change. As another example, additionally or alternatively, a gradient algorithm may identify a local maximum and/or minimum pixel brightness at the pleural position to identify the lower and upper borders of the pleural line in each image. In some embodiments, a deep learning model trained for real-time or static (e.g., not real-time) pleura detection is used to identify the bottom edge of the pleura.

The lower and upper borders of the pleura may include sub pleural consolidations. For example, the bottom edge (e.g., indicating boundary below which to remove ultrasound data, as further described herein) may be positioned a predetermined distance towards the lung from the pleural line. It may be understood that, conventionally, sub pleural consolidations extend a maximum distance 'n' from the pleural surface towards the lung. Thus, the bottom edge of the pleura may be positioned a distance 'n' from the lower border of the pleura identified as described above. In other embodiments, sub pleural consolidations may be identified using the same or a different edge detection algorithm described above. Example 2D ultrasound images including indicators of the pleural line are described with respect to FIGS. 4 and 5.

Briefly turning to FIG. 4, an example annotated 2D lung ultrasound image 400, which may be output to a display as further described with respect to FIG. 3, is shown. The example annotated 2D lung ultrasound image 400 includes a 2D lung ultrasound image 402, which may be generated at operation 306 of the method 300, and pleural line indicators 404, which may be generated at operation 308 of the method 300. The pleural line indicators 404 may be positioned on a bottom edge (e.g., lower boundary) of the pleural line and may visually indicate pixels of the 2D lung ultrasound image 402 which are identified as the pleural line. For example, a pleural line 406 is indicated by the pleural line indicators 404. In other examples, the pleural line 406 may be traced (e.g., with a continuous line) to visually indicate the pleural line 406 in the annotated 2D lung ultrasound image 400.

A vertical location of each of the pleural line indicators 404 may be different and may reflect a curvature, protrusion, cavity, and/or other irregularities in the pleural line. For example, a first pleural indicator 410 may have a higher vertical location relative to a second pleural indicator 412. An orientation of the 2D lung ultrasound image 402 is such that an outside of a patient is towards the top of the image and an inside of a lung of the patient is towards the bottom of the image. Ultrasound imaging data vertically below the pleural line 406 (e.g., below each of the pleural line indicators 404 and spaces therebetween) may be noise and thus may not indicate a topography of the pleural line.

Returning to FIG. 3, following identification of the bottom edge, at 310 the method 300 includes removing ultrasound data from below the bottom edge of the pleura in each ultrasound image. As described with respect to FIG. 4, ultrasound imaging data vertically below the bottom edge of the pleural line may be noise that does not indicate the topography of the pleural line. As described above, sub pleural consolidations are included in the boundary defined by the bottom edge. Removing ultrasound data from below the bottom edge may expose the topography of the pleural line. Removing ultrasound data may include generating a new dataset for each ultrasound image, the new dataset including ultrasound data above and including the pleural line, and excluding data below the bottom edge of the pleural line (e.g., noise).

At 312, the method 300 includes generating a 3D pleural surface based on the 2D ultrasound images. In some examples, operation 312 may be performed prior to operation 310 (e.g., removing ultrasound data from below the bottom edge of the pleural line), as further described with respect to FIG. 5. Described herein are two methods for generating the 3D pleural surface, however additional and/or alternate methods for generating the 3D pleural surface from 2D ultrasound images may be used without departing from the scope of the present disclosure. Both methods described herein generate the 3D pleural surface from volumetric ultrasound data. At 314, the method 300 includes stacking the series of 2D ultrasound images to generate the 3D pleural surface. For example, the series of 2D ultrasound images may include more than 100 2D ultrasound images generated from data captured by positioning the 2D probe over different overlapping or non-overlapping regions of a patient area and acquiring ultrasound data in accordance with the lung ultrasound protocol. Each of the series of 2D ultrasound images may capture a different view of the same patient area, such that topography of the pleural line (e.g., protrusions into the lung, cavities extending away from the lung) may be shown from a different perspective in each 2D ultrasound image. Stacking the series of 2D ultrasound images may include aligning the pleural line shown in each 2D ultrasound image (e.g., aligning respective pleural line indicators 404 in each image) to simulate a 3D ultrasound image.

Figure 5:
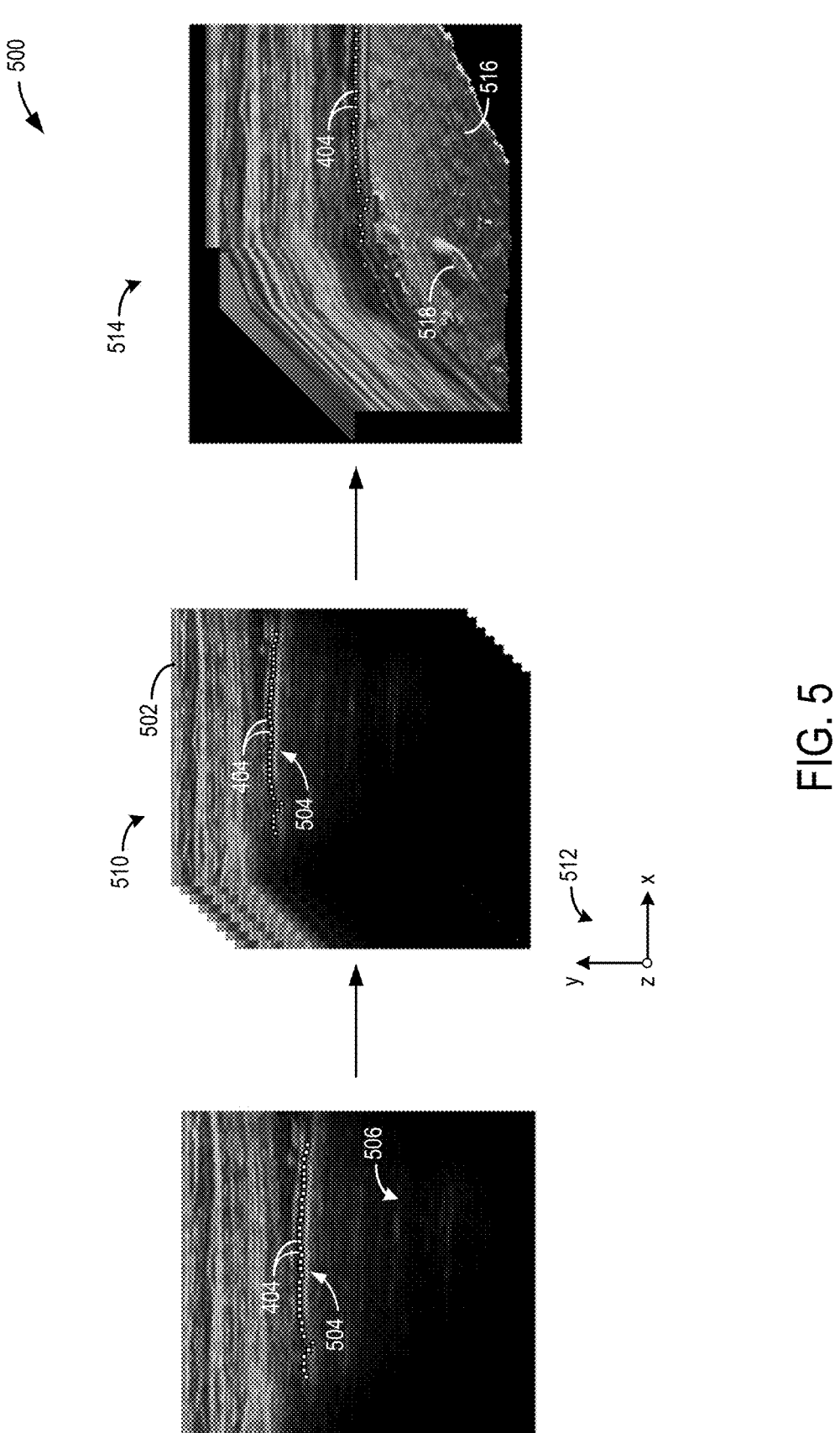
FIG. 5 shows an example method for generating 3D pleural surfaces by stacking 2D ultrasound images, according to an embodiment.

Turning to FIG. 5, an example method 500 for stacking a series of 2D ultrasound images to generate a 3D pleural surface is shown. A 2D ultrasound image 502 is shown as an example one of a series of 2D ultrasound images. The 2D ultrasound image 502 includes pleural line indicators 404, indicating a pleural line 504. Ultrasound data from below the bottom edge of the pleural line 504 has not been removed, therefore the 2D ultrasound image 502 includes noise 506 below the pleural line 504. It is to be understood that other 2D ultrasound images of the series of 2D ultrasound images similarly include pleural line indicators, and ultrasound data from below the pleural line has not been removed. A stack of 2D ultrasound images 510 includes the series of 2D ultrasound images which capture the same patient area from different views, with the 2D ultrasound image 502 on the top of the stack. Each of the 2D ultrasound images below the 2D ultrasound image 502 may be aligned with the 2D ultrasound image 502 along the pleural line 504. For example, respective pleural line indicators 404 may be aligned in space (e.g., same x, y, and z coordinates, with respect to a reference axis system 512). The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples. To form a 3D pleural surface 514, the stack of 2D ultrasound images 510 may be processed to turn the series of 2D ultrasound images 510 into a single, continuous 3D image. Additionally, ultrasound data from below the bottom edge of the pleural line 504 (e.g., noise) may be removed to expose a pleural surface 516. The pleural surface 516 is shown from an inside of the lung looking outward. For example, the outside of the patient is towards the top of the image and an inside of the lung of the patient is towards the bottom of the image. As shown in FIG. 5, the pleural surface 516 may include protrusions, such as a protrusion 518 into the inside of the lung. As further described with respect to FIG. 7, the protrusion 518 may be indicated by comparing pleural line indicators 404. Also, as further described with respect to FIGS. 3 and 7-11, the 3D pleural surface 514 may be shaded by at least one virtual light source to highlight protrusions of the pleural surface 516.

Returning to FIG. 3, at 316, the method 300 includes generating a 3D mesh from the series of 2D ultrasound images and using the 3D mesh to generate the 3D pleural surface. Generating the 3D mesh may include identifying coordinate points in space, for example with respect to an x, y, and z axis system, of the pleural line in each of the series of 2D ultrasound images. For example, each of the series of 2D ultrasound images may be the same size (e.g., the same length, width, number of pixels, etc.), however due to the above described positioning of the 2D probe to acquire ultrasound data, coordinate points of the pleural line may be different in different images of the series of 2D ultrasound images. Each 2D ultrasound image may be positioned on an axis system at the same position (e.g., with a bottom right corner at (0,0)) and coordinates of each pleural line indicator may be identified. A 3D mesh may be constructed using coordinates of each respective pleural line indicator for each of the series of 2D ultrasound images, as further described with respect to FIG. 6.

Figure 6:
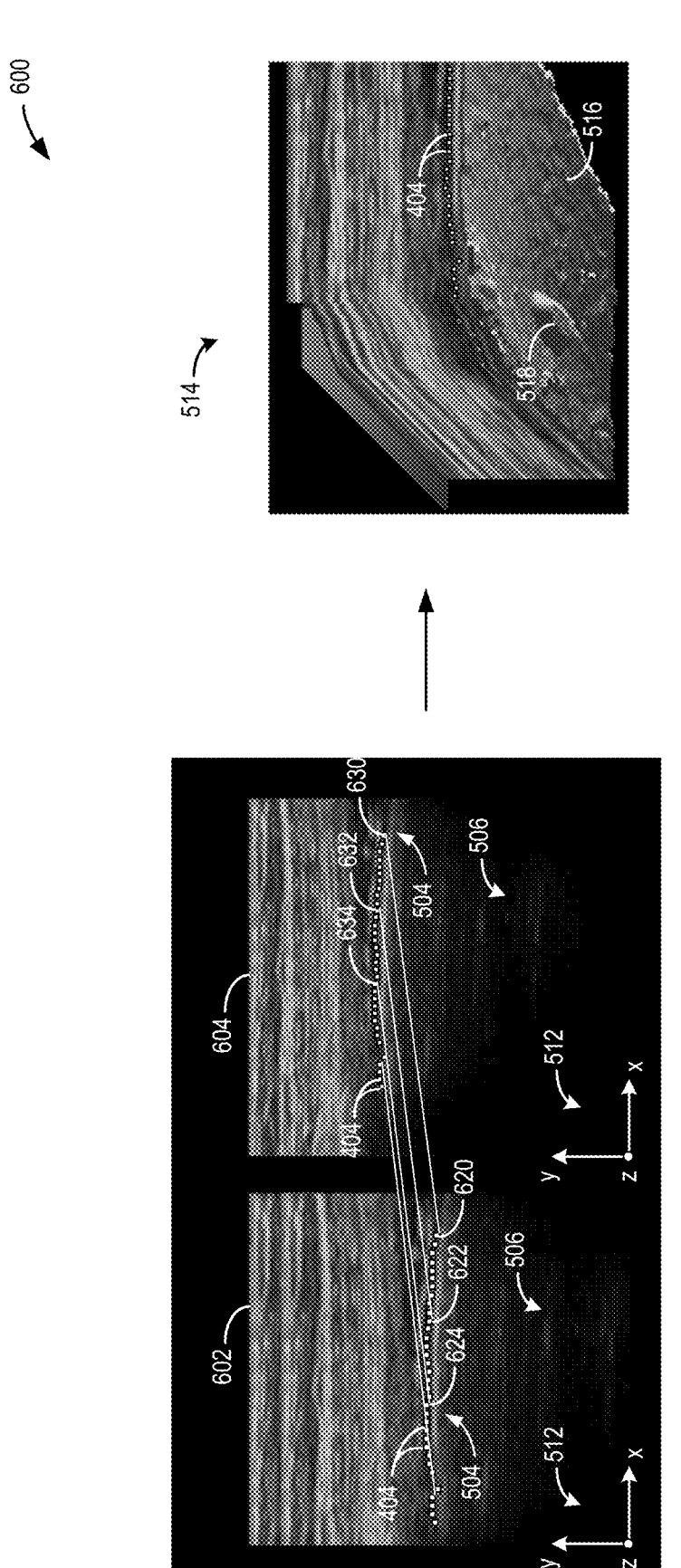
FIG. 6 shows an example method for generating 3D pleural surfaces by generating a 3D mesh from 2D ultrasound images, according to an embodiment.

Turning to FIG. 6, an example method 600 for generating a 3D pleural surface from a 3D mesh based on a series of 2D images is shown. A first 2D ultrasound image 602 and a second 2D ultrasound image 604 may be included in a series of 2D ultrasound images. Each of the first 2D ultrasound image 602 and a second 2D ultrasound image 604 includes pleural line indicators 404 indicating the pleural line 504. Ultrasound data from below the pleural line 504 has not been removed in either image, therefore the first 2D ultrasound image 602 and the second 2D ultrasound image 604 include noise 506 below the pleural line 504. It is to be understood that other 2D ultrasound images of the series of 2D ultrasound images similarly include pleural line indicators and ultrasound data from below the pleural line has not been removed.

As described with respect to FIG. 3, each of the first 2D ultrasound image 602 and the second 2D ultrasound image 604 may have the same dimensions (e.g., length and width) and may capture different views of a lung region (e.g., the pleural line 504). The first 2D ultrasound image 602 and the second 2D ultrasound image 604 are each aligned to the reference axis system 512. For example, a bottom left corner of each image is positioned at (0,0). To generate a 3D mesh, the pleural line 504 in the first 2D ultrasound image 602 is mapped to the pleural line 504 in the second 2D ultrasound image 604. For example, a first pleural indicator 620, a second pleural indicator 622, and a third pleural indicator 624 of the first 2D ultrasound image are each mapped to a fourth pleural indicator 630, a fifth pleural indicator 632, and a sixth pleural indicator 634, respectively, of the second 2D ultrasound image 604. FIG. 6 shows the comparison of two 2D ultrasound images for illustrative purposes, however generating the 3D mesh may include comparing more than two 2D ultrasound images of the series of 2D ultrasound images. For example, the 3D mesh may be generated based on comparison of at least 100 2D ultrasound images of the series of 2D ultrasound images. A 3D mesh, such as a mesh comprised of polygons wherein height, width, and depth of the polygons are defined by coordinate points of the pleural line 504 among the compared series of 2D ultrasound images. The 3D pleural surface 514 may be generated from the 3D mesh, where one or more 2D ultrasound images of the series of 2D ultrasound images are deformed according to a topography of the 3D mesh. The 3D pleural surface 514 thus includes the pleural line 504 and protrusions of the pleural line 504, such as a protrusion 518. As described with respect to FIG. 5, the pleural surface 516 is shown from an inside of the lung looking outward, and the 3D pleural surface 514 may be shaded by at least one virtual light source to highlight protrusions of the pleural surface 516.

Returning to FIG. 3, at 318 the method 300 includes saving the 3D pleural surface to memory and outputting the 3D pleural surface for display on a display device. In some examples, the display is included in the ultrasound imaging system, such as display device 118. The 3D pleural surface may or may not be displayed with annotations indicating the pleural line. Example displays of the 3D pleural surface are shown in FIGS. 8-10. The 3D pleural surface may be saved with and without annotations (e.g., pleural line indicators) in some examples. Further, raw, unprocessed ultrasound data may be saved, at least in some examples. The memory may be local to the ultrasound imaging system or may be a remote memory. For example, the unannotated and annotated images may be saved and/or archived (e.g., as a structured report in a PACS system) so that they may be retrieved and used to generate an official, physician-signed report that may be included in the patient's medical record (e.g., the EHR).

The 3D pleural surface generated as described with respect to FIG. 3 thus includes a more detailed view of the pleura, compared to a 2D ultrasound image of the pleura. A series of 2D ultrasound images (e.g., the series of 2D ultrasound images used to generate the 3D pleural surface) may be used to visualize topography of the pleura which is shown in the single 3D pleural surface. Thus, generating the 3D pleural surface may simplify image analysis by showing detailed topography of the pleura in one image (e.g., the 3D pleural surface), rather than in multiple images (e.g., the series of 2D ultrasound images).

As briefly described with respect to FIGS. 5 and 6, at 320, the method 300 optionally includes applying shading to the 3D pleural surface. The 3D pleural surface may be shaded via at least one virtual light source positioned as if inside the lung. The shading may highlight a protrusion (e.g., the protrusion 518 of FIGS. 5 and 6) extending from the 3D pleural surface towards the inside of the lung. For example, the at least one virtual light source may be positioned at a pre-set location within the inside of the lung, such as at an acute angle with respect to the 3D pleural surface and/or a protrusion therefrom. A position, brightness, color, and/or number of virtual light sources may be adjusted in response to receiving user input. Further detail regarding shading the 3D pleural surface is described with respect to FIG. 7.

Figure 7:
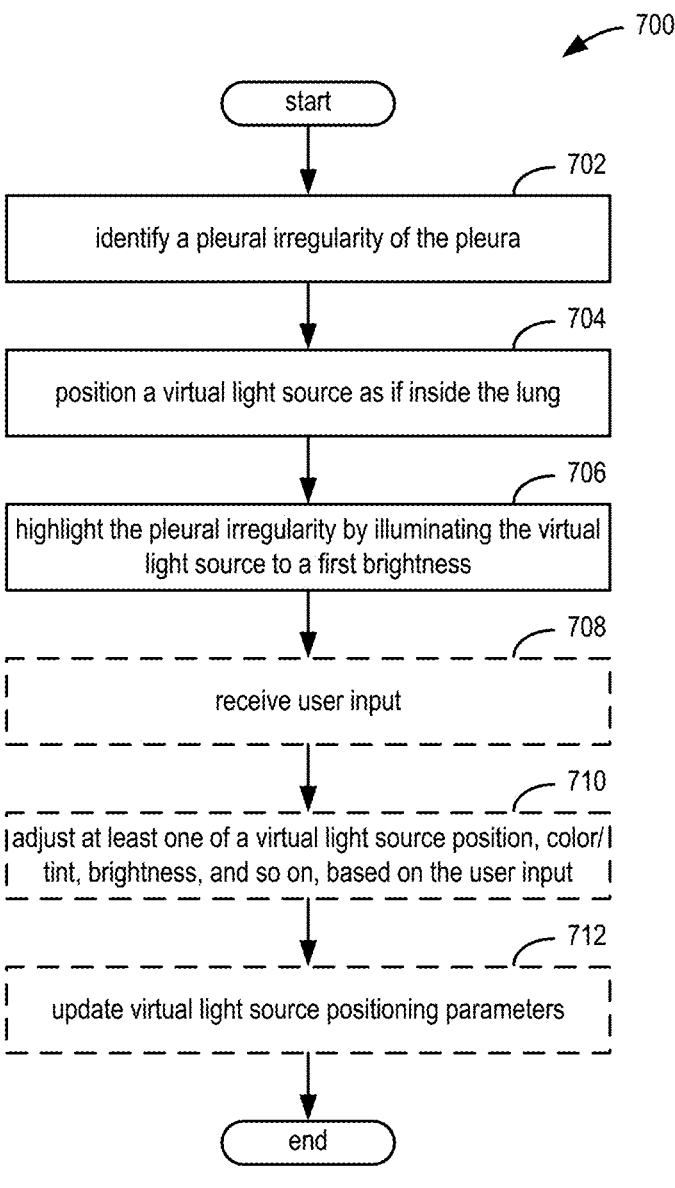
FIG. 7 shows a flowchart illustrating an example method for shading a 3D pleural surface, according to an embodiment.

FIG. 7 shows a flowchart illustrating an example method 700 for shading a 3D pleural surface, for example, the 3D pleural surface generated as described with respect to FIGS. 3 and/or 11. In particular, method 700 provides a workflow for positioning at least one virtual light source as if inside the lung, pointed towards the 3D pleural surface (e.g., from an inside of the lung to an outside of the lung). Method 700 may be implemented by one or more of the above described systems, including the ultrasound imaging system 100 of FIG. 1 and medical image processing system 200 of FIG. 2. As such, method 700 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2.

At 702, the method 700 includes identifying a pleural irregularity of the pleura. For example, the pleural irregularity may a protrusion extending from a 3D pleural surface towards an inside of a lung or a cavity extending into the pleural 3D pleural surface (e.g., from the bottom edge of the pleura, away from the lung). The method 700 may be applied to the 3D pleural surface generated as described with respect to the method 300 of FIG. 3, an example of which may be the 3D pleural surface 514 of FIGS. 5 and 6. For example, the processor may evaluate each pixel of the identified pleura (e.g., within the upper and lower borders of the pleural line) to locally characterize the pleura as either healthy or irregular via pre-determined scoring criteria. As described with respect to FIG. 3, detecting the pleural position may include identifying lower and upper borders of the pleura based on a brightness change between pixels, such as by using edge detection techniques or gradient changes. The processor may evaluate each pixel of the pleural line to determine a jumpiness score and a dimness score for each pleural location in order to identify positions of pleural irregularities. The jumpiness score evaluates a vertical location of the pleural line at each horizontal location to identify vertical gaps in the pleural line, with a greater vertical gap resulting in a higher jumpiness score. For example, the vertical gap may refer to a number of pixels vertically between the lower border (or upper border) of the pleural line at the given pixel location relative to a neighboring pixel. The vertical gap between the upper or lower border of the pleural line at neighboring horizontal locations may result in the pleural line having a discontinuous or rough appearance, for example. The dimness score ranks the pleural pixel brightness (or dimness) at a particular horizontal location relative to its neighbors. As the local pixel brightness of the pleura decreases relative to its neighbors (e.g., the pixel becomes more dim relative to its neighbors), the dimness score increases.

An irregularity score for each pixel along the pleural line in each frame may be generated as a product of the jumpiness score and the dimness score and compared to a threshold score. The threshold score may be a pre-determined value stored in memory that distinguishes irregular pleura associated with a disease state from normal, healthy pleura. In some examples, the threshold score may be adjusted based on curated data and using a support vector machine. If the irregularity score is greater than or equal to the threshold score, the pleura imaged in that pixel location may be considered irregular. In contrast, if the irregularity score is less than the threshold score, the pleura imaged in that pixel location may not be considered irregular (e.g., may be considered normal and/or healthy). Although the pleura may be analyzed on a pixel-by-pixel basis, a filter may be used to smooth the results. As a result, an area of pixels having pre-determined dimensions may be grouped and identified as a location of irregularity (e.g., irregular pleura) responsive to a majority (e.g., greater than 50%) of the pixels within the group being characterized as irregular pleura (e.g., a protrusion). In contrast, the area of pixels may be identified as healthy responsive to the majority of the pixels within the group being characterized as healthy pleura.

Following identification of a pleural irregularity (e.g., a protrusion), at 704 the method 700 includes positioning a virtual light source as if inside the lung. As described with respect to FIGS. 3-6, the 3D pleural surface is viewed from the inside of the lung and looking outward (e.g., a region below the pleural surface 516 in the 3D pleural surface 514 is considered inside the lung). The virtual light source may be positioned such that, when illuminated, the virtual light source directs light towards the pleural surface 516. The virtual light source may be positioned in a pre-set location with respect to the pleural surface, such as a bottom right, top left, bottom left, or top right of a display. In some examples, the virtual light source may be positioned with respect to the identified protrusion. For example, when the identified protrusion is in a top left quadrant of a display, the virtual light source may be positioned in a bottom right quadrant of the display. At 706, the method 700 includes highlighting the pleural irregularity by illuminating the virtual light source to a first brightness. The virtual light source may emit light radially, linearly, or as a ray, for example, and a shape of emitted light may be adjusted in response to user input, as further described herein. A brightness and a color/tint of the virtual light source may further be adjusted in response to user input, as further described herein.

Turning briefly to FIG. 8, a first example 3D lung model 800 is illustrated, which is output to a display 801. The display 801 may be the display device 118 of FIG. 1, for example. As further described with respect to FIG. 7, the display 801 includes sliders for adjusting a brightness (e.g., a brightness slider 810), a color/tint (e.g., hue boxes 812), and a position (e.g., a coordinate selector 814) of one or more light sources, as well as a reference axis system 890. The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples.

The first example 3D lung model 800 includes a windpipe (e.g., trachea) 802, a left lung 804, and a right lung 806. The left lung 804 is illustrated as a cross-section (e.g., taken along a y-x plane, with respect to the reference axis 890) showing an inside 808 and a pleura 816 of the left lung 804. In other embodiments of the 3D lung model 800, the right lung 806 may additionally or alternatively be illustrated as a cross-section. A 3D pleural surface (e.g., the 3D pleural surface 514) is overlaid on the left lung 804 in an approximate anatomical position and orientation such that the pleural line of the 3D pleural surface is aligned with the pleura 816 of the left lung 804. For example, the 3D pleural surface 514 may be generated from imaging data captured of the left lung 804 at an approximate location where the 3D pleural surface is overlaid on the left lung 804 in the display 801. The pleural surface 516 is shown exposed to an interior of the left lung 804. Although only one 3D pleural surface is shown in the example of FIG. 8, additional generated 3D pleural surfaces may be positioned on different locations of the first example 3D lung model 800, such as on a back of the left lung 804, a side of the left lung 804, a front of the right lung 806, a back of the right lung 806, or a side of the right lung 806. Further, although not explicitly shown in FIG. 8, the 3D pleural surface may include annotations, as described above.

As described with respect to FIG. 7, a virtual light source 820 may be positioned within the inside 808 of the lung (e.g., the left lung 804) and be used to shade the 3D pleural surface 514. In some examples, the virtual light source 820 may be automatically positioned at pre-set or random coordinates within the inside of the lung which corresponds with the 3D pleural surface 514. Coordinates of the virtual light source may be shown in the coordinate selector 814. The virtual light source 820 may be positioned with respect to an identified protrusion in the 3D pleural surface 514 (e.g., which extends towards the inside 808 of the lung. For example, as described with respect to FIG. 7, one or more protrusions of the 3D pleural surface 514 may be identified, and the virtual light source 820 may be positioned at coordinates where the virtual light source 820, and light beam (e.g., indicated by an arrow 822) cast by the virtual light source 820, is at an acute angle with respect to the 3D pleural surface 514. In this way, the virtual light source 820 may highlight the protrusion extending from the pleural surface 516 towards the inside 808 of the left lung 804. This may assist a user, such as a healthcare provider or imaging technician viewing the display 801 to quickly and accurately identify pleural irregularities in the 3D pleural surface, which may help reduce a diagnosis timeline and increase an accuracy of diagnosis.

Turning to FIG. 9, a second example 3D lung model 900 is illustrated, which is output to the display 801, as described with respect to FIG. 8. The second example 3D lung model 900 may include a 3D pleural surface (e.g., the 3D pleural surface 514) centered on a quadrant grid and oriented such that an outside of a patient is in an upper right and an upper left quadrant, and an inside of a lung of the patient is in a bottom right and a bottom left quadrant of the quadrant grid. Automatically positioning the virtual light source 820 may include identifying a protrusion, as described with respect to FIG. 7, and positioning the virtual light source 820 in a complementary quadrant. For example, when the protrusion 518 is in the bottom left quadrant, the virtual light source 820 may be automatically positioned in the bottom right quadrant, such that the light beam, indicated by the arrow 822, highlights at least part of the protrusion 518. In examples where a protrusion is in the bottom right quadrant, the virtual light source 820 may be positioned in the bottom left quadrant. In some examples, the virtual light source 820 may be automatically positioned without identifying a protrusion. The virtual light source 820 may be positioned at pre-set or random coordinates in one of the bottom right or the bottom left quadrants. As further described with respect to FIG. 7, the virtual light source 820 may be moved in response to a user input, such as changing coordinates of the virtual light source 820 in the coordinate selector 814, selecting and moving the virtual light source 820 (e.g., dragging a selection tool across the display 801), selecting on the display 801 a new position for the virtual light source 820, and so on. As described with respect to FIG. 8, the second example 3D lung model 900 may assist a user to quickly and accurately identify pleural irregularities in the 3D pleural surface.

Turning to FIG. 10, an example lung model 1000 is illustrated, which is output to the display 801, as described with respect to FIGS. 8 and 9. The example lung model 1000 may include a 3D pleural surface (e.g., the 3D pleural surface 514) and a representative 2D image used to generate the 3D pleural surface (e.g., the 2D ultrasound image 502), which may be displayed simultaneously in an image window 1002. As described with respect to FIG. 9, the 3D pleural surface 514 may be centered on a quadrant grid and oriented such that the outside of the patient is in the upper right and the upper left quadrant, and the inside of the lung of the patient is in the bottom right and the bottom left quadrant of the quadrant grid. The 3D pleural surface 514 may be a live 3D surface rendering of the detected pleura, or may be a static image provided following data collection using the ultrasound probe. The virtual light source 820 may be automatically positioned as described with respect to FIGS. 7-9. The 2D ultrasound image 502 may be included in the example lung model 1000 to show a reference image from which the 3D pleural surface 514 was generated (e.g., as described with respect to FIGS. 3 and 11), which may assist in pleural irregularity identification and diagnosis. For example, the 2D ultrasound image 502 may be a live B-mode slice which may be automatically selected or selected by a user via interacting with a user interface (e.g., the user interface 115).

Returning to FIG. 7, in some examples, the method 700 may include receiving user input at 708 and adjusting the display accordingly. For example, the user input may include inputting x, y, and/or z coordinates (e.g., into the coordinate selector 814 of FIGS. 8-10) via a user interface (e.g., the user interface 115) to update a position of a virtual light source. In some examples, a user may select and the virtual light source on the display (e.g., click, drag, and release, or select current location, then select new location). The user input may additionally or alternatively include adjustment to a brightness of the virtual light source, such as selection of a new brightness from brightness options, inputting a new brightness, increasing/decreasing the brightness using a slider bar (e.g., the brightness slider 810 of FIGS. 8-10), and so on. Additionally or alternatively, the user input may include adjustment to a color/tint of the virtual light source, for example, adjusting from white light to colored light or adjusting an amount of red, blue, and/or green light (e.g., using the hue boxes 812). The user input may include adding one or more additional virtual light sources, which may have a default position, color/tint, brightness, and so on when added. Characteristics of additional virtual light sources (e.g., position, color/tint, brightness, etc.) may be individually adjusted as described above. At 710, the method 700 includes adjusting at least one of a virtual light source position, color/tint, brightness, and so on, based on the user input.

Following adjustment based on user input, at 712, the method 700 may include updating virtual light source positioning parameters. For example, the method 700 may use an algorithm to automatically position a virtual light source prior to receiving user input. Following receipt of user input, the algorithm may be updated to revise initial positioning of the virtual light source based on user input. For example, the algorithm may learn common user selections of parameters including color/tint, brightness, position, etc., and apply the parameters when automatically positioning a virtual light source during following implementations of the method 700.

Figure 11:
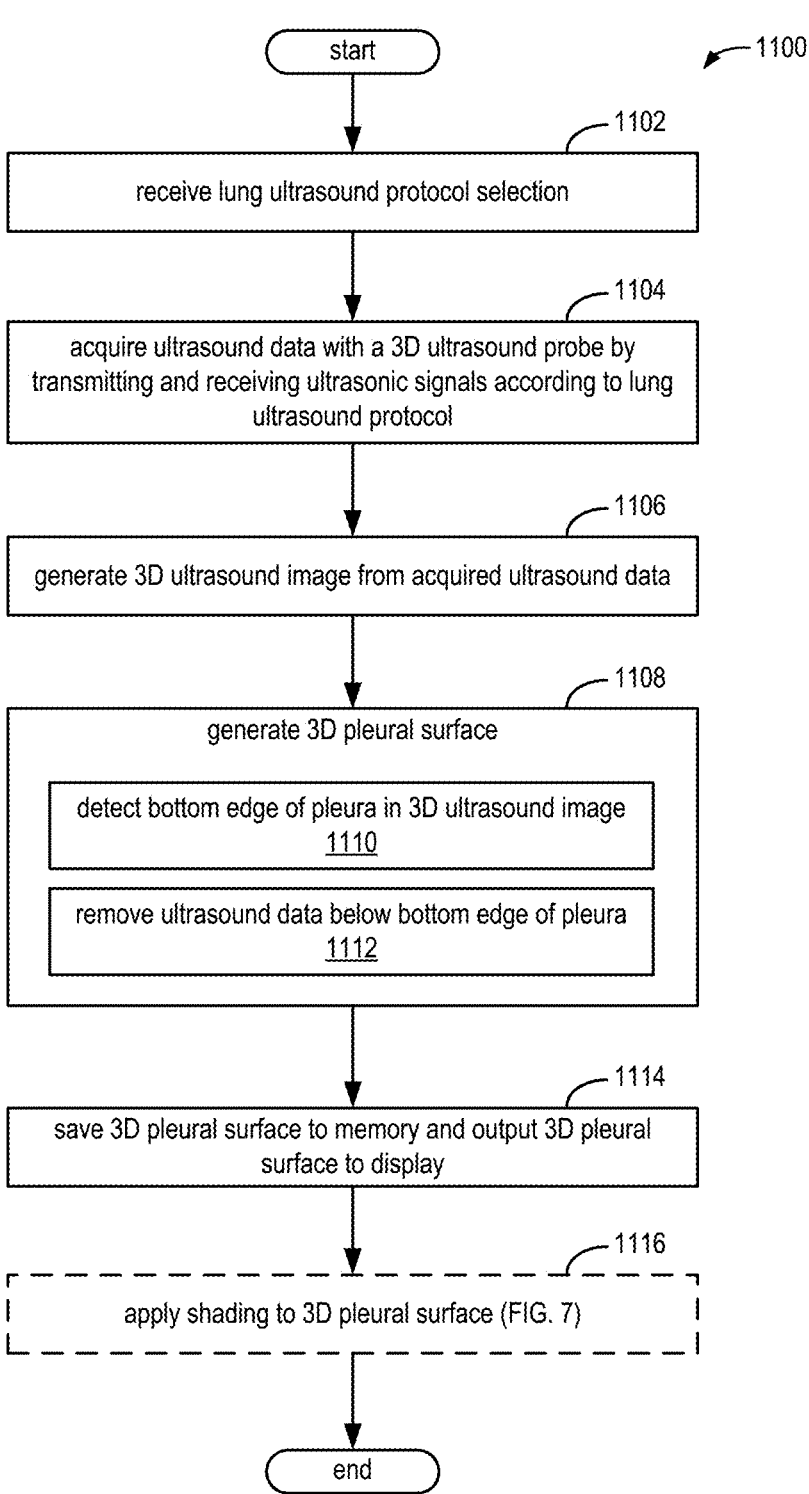
FIG. 11 shows a flowchart illustrating an example method for generating 3D pleural surfaces from 3D ultrasound images, according to an embodiment.

In this way, the method 700 provides shading to 3D pleural surfaces, which may be generated according to the methods of FIGS. 3 and 11, which highlights pleural irregularities such as protrusions into an inside of a lung, thus making the pleural irregularities more visible on a display compared to an unshaded 3D pleural surface. A mental burden on the operator may be decreased. Additionally, a variability between operators in pleural irregularity detection accuracy and frequency is decreased. Overall, an accuracy of a diagnosis may be increased while an amount of time before the diagnosis is made may be decreased.

FIG. 11 shows a flow chart for an additional example method 1100 for generating a 3D pleural surface (e.g., the 3D pleural surface 514 of FIGS. 5-6 and 8-10), where ultrasound imaging signals used to generate the 3D pleural surface are acquired using a probe capable of live 3D imaging, such as a matrix array probe or other volumetric probe, to acquire a 3D volume. In particular, the method 1100 provides a workflow for generating the 3D pleural surface from a 3D image captured using the probe capable of live 3D imaging by identifying a pleural line in the 3D image and segmenting the 3D image at the pleural line to expose the 3D pleural surface. Method 1100 will be described for 3D ultrasound images acquired using an ultrasound imaging system, such as ultrasound imaging system 100 of FIG. 1, although other ultrasound imaging systems may be used. Further, method 1100 may be adapted to other imaging modalities. Method 1100 may be implemented by one or more of the above described systems, including the ultrasound imaging system 100 of FIG. 1 and medical image processing system 200 of FIG. 2. As such, method 1100 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. Further, in some embodiments, method 1100 is performed in real-time, as the 3D image is acquired, while in other embodiments, at least portions of method 1100 are performed offline, after the 3D image is acquired. For example, the processor may evaluate 3D images that are stored in memory even while the ultrasound system is not actively being operated to acquire images.

At 1102, method 1100 includes receiving a lung ultrasound protocol selection. The lung ultrasound protocol may be selected by an operator (e.g., user) of the ultrasound imaging system via a user interface (e.g., the user interface 115). As one example, the operator may select the lung ultrasound protocol from a plurality of possible ultrasound protocols using a drop-down menu or by selecting a virtual button. Alternatively, the system may automatically select the protocol based on data received from an EHR associated with the patient. For example, the EHR may include previously performed exams, diagnoses, and current treatments, which may be used to select the lung ultrasound protocol. Further, in some examples, the operator may manually input and/or update parameters to use for the lung ultrasound protocol. The lung ultrasound protocol may be a system guided protocol, where the system guides the operator through the protocol step-by-step, or a user guided protocol, where the operator follows a lab-defined or self-defined protocol without the system enforcing a specific protocol or having prior knowledge of the protocol steps.

Further, the lung ultrasound protocol may include a plurality of scanning sites (e.g., views), probe movements, and/or imaging modes that are sequentially performed. For example, the lung ultrasound protocol may include using dynamic M-mode. The lung ultrasound protocol may include a longitudinal scan, wherein the probe is positioned perpendicular to the ribs, and/or an oblique scan, wherein the probe is positioned along intercostal spaces between ribs. Further still, in examples where the ultrasound probe is a matrix probe, the lung ultrasound protocol may include indicating a static position on the patient at which to hold the ultrasound probe while volumetric ultrasound data is captured by the ultrasound probe.

At 1104, method 1100 includes acquiring ultrasound data with the ultrasound probe by transmitting and receiving ultrasonic signals according to the lung ultrasound protocol. Acquiring ultrasound data according to the lung ultrasound protocol may include the system displaying instructions on the user interface, for example, to guide the operator through the acquisition of the designated scanning sites. Additionally or alternatively, the lung ultrasound protocol may include instructions for the ultrasound system to automatically acquire some or all of the data or perform other functions. For example, the lung ultrasound protocol may include instructions for the user to position, move, rotate, tilt, and/or sweep the ultrasound probe, as well as to automatically initiate and/or terminate a scanning process and/or adjust imaging parameters of the ultrasound probe, such as ultrasound signal transmission parameters, ultrasound signal receive parameters, ultrasound signal processing parameters, or ultrasound signal display parameters. In some embodiments, live 3D image data may be acquired by a matrix 2D probe, or by a mechanically-wobbling 1D probe. Further, the acquired ultrasound data include one or more image parameters calculated for each pixel or group of pixels (for example, a group of pixels assigned the same parameter value) to be displayed, where the one or more calculated image parameters include, for example, one or more of an intensity, velocity, color flow velocity, texture, graininess, contractility, deformation, and rate of deformation value.

At 1106, method 1100 includes generating a 3D ultrasound image from the acquired ultrasound data. For example, the signal data acquired during the method at 1104 is processed and analyzed by the processor in order to produce a 3D ultrasound image at a designated frame rate. The processor may include an image processing module that receives the signal data (e.g., image data) acquired at 1104 and processes the received image data. For example, the image processing module may process the ultrasound signals to generate a 3D volumetric rendering of ultrasound information for displaying to the operator. In one example, generating the 3D ultrasound image may include determining an intensity value for each pixel to be displayed based on the received image data.

At 1108 the method 1100 includes generating a 3D pleural surface from the 3D ultrasound image. Generating the 3D pleural surface may be performed in two steps. At 1110, the method 1100 includes detecting a bottom edge of the pleura in the 3D ultrasound image. In an aerated lung, the pleura, which form the outer boundary of the lung that lies against the chest wall, may provide the substantially only anatomical lung structure detectable by ultrasound. The pleura appear as a hyperechoic horizontal segment of brighter (e.g., whiter) pixels in the 3D ultrasound image, referred to as a pleural line, which moves synchronously with respiration in a phenomenon known as pleural sliding. Detecting the pleural position may include identifying lower and upper borders of the pleura based on a brightness change between pixels, such as by using edge detection techniques or gradient changes. For example, the processor may apply an edge detection algorithm, such as included in the 3D generation module 212 of FIG. 2, that comprises one or more mathematical methods for identifying points (e.g., pixels) at which the image brightness changes sharply and/or has discontinuities to identify the lower and upper borders of the pleural line. As one example, the processor may apply the edge detection algorithm to the area having the highest amount of local change. As another example, additionally or alternatively, a gradient algorithm may identify a local maximum and/or minimum pixel brightness at the pleural position to identify the lower and upper borders of the pleural line in each image. In frames without pleural sliding (e.g., between breaths), the location of the pleura may be tracked up/down based on its known location from the previous frame.

The lower and upper borders of the pleura may include sub pleural consolidations. For example, the bottom edge (e.g., indicating boundary below which to remove ultrasound data, as further described herein) may be positioned a predetermined distance towards the lung from the pleural line. It may be understood that, conventionally, sub pleural consolidations extend a maximum distance 'n' from the pleural surface towards the lung. Thus, the bottom edge of the pleura may be positioned a distance 'n' from the lower border of the pleura identified as described above. In other embodiments, sub pleural consolidations may be identified using the same or a different edge detection algorithm described above.

Following identification of the pleural position, at 1112, method 1100 includes removing ultrasound data from below the bottom edge of the pleural line in the 3D ultrasound image. As described with respect to FIG. 4, ultrasound imaging data vertically below the bottom edge of the pleural line may be noise that does not indicate the topography of the pleural line. Removing ultrasound data from below the bottom edge of the pleural line may expose the topography of the pleural line. Removing ultrasound data may include generating a new dataset for each ultrasound image, the new dataset including ultrasound data above and including the pleural line, and excluding data below the bottom edge of the pleural line (e.g., noise).

Turning briefly to FIG. 12, an example set of images 1200 is shown, including a 3D ultrasound image 1202 and a 3D pleural surface 1204. The 3D ultrasound image 1202 may be an example of the 3D ultrasound image generated from ultrasound data acquired using a volumetric probe (e.g., at operation 1106 of method 1100). The 3D pleural surface 1204 may be generated from the 3D ultrasound image, as described with respect to the method 1100. Each of the 3D ultrasound image 1202 and the 3D pleural surface 1204 may include pleural line indicators 1206, which may be generated at operation 1108 of the method 1100. The pleural line indicators 1206 may be positioned on a lower boundary (e.g., the bottom edge) of the pleural line and may visually indicate pixels of the 3D ultrasound image 1202 which are identified as the pleural line. In other examples, the pleural line may be traced (e.g., with a continuous line) to visually indicate the pleural line in the 3D ultrasound image 1202. Removing ultrasound data from below the pleural line may include removing ultrasound data below the pleural line indicators 1206. As a vertical location of each of the pleural line indicators 1206 may be different and may reflect a curvature, protrusion, and/or other irregularities in the pleural line, removal of ultrasound data below the pleural line indicators 1206 results in a topographical pleural surface 1216 which includes protrusions into the inside of the lung, such as a protrusion 1218.

Returning to FIG. 11, following generation of the 3D pleural surface at operation 1108, at 1114, the method 1100 includes outputting the 3D pleural surface for display on a display device. In some examples, the display is included in the ultrasound imaging system, such as display device 118. The 3D pleural surface may or may not be displayed with annotations indicating the pleural line. Example displays of the 3D pleural surface are shown in FIGS. 8-10. The 3D pleural surface may be saved with and without annotations (e.g., pleural line indicators) in some examples. Further, raw, unprocessed ultrasound data may be saved, at least in some examples. The memory may be local to the ultrasound imaging system or may be a remote memory. For example, the unannotated and annotated images may be saved and/or archived (e.g., as a structured report in a PACS system) so that they may be retrieved and used to generate an official, physician-signed report that may be included in the patient's medical record (e.g., the EHR).

At 1116, the method 1100 optionally includes applying shading to the 3D pleural surface. The 3D pleural surface may be shaded via at least one virtual light source positioned as if inside the lung. The shading may highlight a protrusion (e.g., the protrusion 1218 of FIG. 12) extending from the 3D pleural surface towards the inside of the lung. At least one virtual light source may be positioned to apply shading to the 3D pleural surface as described with respect to FIG. 7. For example, the at least one virtual light source may be positioned at a pre-set location within the inside of the lung, such as at an acute angle with respect to the 3D pleural surface and/or a protrusion therefrom. A position, brightness, color, and/or number of virtual light sources may be adjusted in response to receiving user input.

The 3D pleural surface generated as described with respect to FIG. 11 includes a more detailed view of the pleura, compared to a 2D ultrasound image of the pleura. As the 3D pleural surface is generated from volumetric ultrasound data captured using a volumetric probe, a number of scans performed to capture the volumetric ultrasound data may be reduced compared to a number of scans used to capture a series of 2D ultrasound images used to generate the 3D pleural surface (e.g., as described with respect to FIG. 3). Thus, a processing power demand on the image processing system may be reduced, as volumetric data is acquired by the ultrasound probe.

The methods described with respect to FIGS. 3, 7, and 11 for generating a 3D pleural surface may be expanded upon to provide further automatic identification and highlighting of pleural surface features and irregularities. For example, methods may be employed which enable surface-based scoring of irregularities and B-lines that indicate a potential severity of pleural irregularities, which may assist in patient diagnosis. Additionally, conventional auto B-line algorithms may be extended to the 3D pleural surface and used to identify and display B-lines for the 3D pleural surface, enabling B-lines to be displayed graphically in 3D. For example, this may include volume-rendering B-lines based on detected pleural irregularities (e.g., protrusions from the pleural surface towards an inside of a lung). Conventional auto B-line algorithms may further be extended into other pathologies which may be shown in the 3D pleural surface, such as consolidations and pleural effusion. Additionally, the generated 3D pleural surface may be used for identification of pneumothorax (PTX). For example, a lung point (e.g., an edge of PTX) is shown as a contour of the 3D pleural surface, which may be highlighted using the virtual light source described with respect to FIGS. 7-10.

FIG. 13 shows a fourth example display 1300, including biplane and 3D images of a lung, including a pleural surface. The images of the fourth example display 1300 may be obtained using a method which leverages existing 3D ultrasound imaging technology, such as the method 1100 described with respect to FIG. 11. An orientation view 1302 shows a 3D imaged region 1308 (e.g., a lung), and includes a first plane 1304 and a second plane 1306 indicating biplane cross-sections of the 3D imaged region 1308. A first 2D planar view 1310 shows the 3D imaged region 1308 segmented by the first plane 1304. A second 2D planar view 1320 shows the 3D imaged region 1308 segmented by the second plane 1306. The first and second 2D planar views 1310, 1320 are segmented by different planes to show different regions of the lung, including different regions of the pleural surface.

Each of the first and second 2D planar views 1310, 1320 include a line 1312 which is approximately used to section the 2D image to enable visualization of topography of the 3D pleural surface. For example, the line 1312 is shown as a linear line, however sectioning of the 3D pleural surface may be non-linear and instead show a 3D topography of the 3D pleural surface, including protrusions and cavities. The first and second 2D planar views 1310, 1320 additionally include B-lines which may indicate irregularities in the pleural surface, such as protrusions and/or cavities. A linear white line 1314 may indicate the pleural line. In the first 2D planar view 1310, a first B-line 1316 extends from the linear white line 1314 towards the line 1312. In the second 2D planar view 1320, a second B-line 1318, a third B-line 1320, and a fourth B-line 1322 all extend towards the line 1312. In some examples, the third B-line 1320 may represent the same pleural irregularity represented by the first B-line 1316, as viewed from a different perspective.

A first arrow 1324 and a second arrow 1326 may indicate a positioning and a direction of one or more virtual light sources used to highlight the 3D pleural surface image 1330.

The one or more virtual light sources may be positioned as described with respect to FIG. 7.

A 3D pleural surface image 1330 may be formed from the 3D imaged region 1308 by removing ultrasound data including noise and non-pleural surface topography, for example as described with respect to FIGS. 3 and 11. The 3D pleural surface image 1330 shows a topography of the pleural surface, including protrusions and cavities of the pleural line. In the first and second 2D planar views 1310, 1320, these protrusions and cavities of the pleural line are shown as B-lines. However, while pleural irregularities and other pathologies are visible in the 2D planar views, due to the 2D nature of the 2D planar views, some characteristics of the pleural irregularities and other pathologies may be excluded. It may be challenging for an observer of the 2D planar views to appreciate an entire pleural surface, including 3D topography of the pleural line and irregularities thereof, compared to the 3D pleural surface image 1330. For example, a protrusion from the pleural surface, enclosed in circle 1332, may be indicated in the first and second 2D planar views 1310, 1320 by the first B-line 1316 and the second B-line 1320 respectively. The 3D pleural surface image 1330 shows the protrusion in further detail, which may assist in identification and diagnosis of pleural irregularities and other pathologies.

In this way, a processor may automatically generate a 3D pleural surface of a lung pleura viewed from an inside of a lung and looking outward based on ultrasound imaging signals. The methods and systems described herein enable visualization of an entire pleural surface which is captured by an ultrasound probe, as opposed to a representative 2D image which may or may not include pathologies present and/or extending into 3D space. This may eliminate a diagnostic step of searching for specific views of the pleural surface. In this way, a wide range of ultrasound findings and pathologies may be visualized, including pleural irregularities, pneumothorax, and viral and bacterial infections. As a result, an amount of time the healthcare professional spends reviewing the medical images may be reduced, enabling the healthcare professional to focus on patient care and comfort. Further, by including the 3D pleural surface overlaid on a 3D rendering of a lung model, the pleural irregularities may be displayed in an anatomically relevant environment in order to further simplify a diagnostic process.

A technical effect of generating a 3D pleural surface of a lung pleura viewed from an inside of a lung and looking outward is that a processing power used by an imaging system may be reduced due to a reduced number of additional imaging scans as a result of increased accuracy and detail of pleural surface image renderings.

The disclosure also provides support for a method for imaging a lung of a patient, comprising: generating a three-dimensional (3D) pleural surface viewed from an inside of the lung and looking outward based on ultrasound imaging signals. In a first example of the method, ultrasound imaging signals are captured by positioning a one-dimensional (1D), 1.5-dimensional (1.5D), or matrix (two-dimensional, 2D) probe to acquire a 2D image. In a second example of the method, optionally including the first example, ultrasound imaging signals are captured by positioning a probe capable of live 3D imaging to acquire volumetric data. In a third example of the method, optionally including one or both of the first and second examples, the method further comprises: generating an ultrasound image from ultrasound imaging signals, detecting a bottom edge of a pleura in the ultrasound image, and removing ultrasound data from below the bottom edge of the pleura. In a fourth example of the method, optionally including one or more or each of the first through third examples, the method further comprises: shading the 3D pleural surface via at least one virtual light source positioned as if inside the lung at an acute angle relative to the 3D pleural surface. In a fifth example of the method, optionally including one or more or each of the first through fourth examples, the shading comprises: highlighting a pleural irregularity of the 3D pleural surface and positioning the at least one virtual light source within the inside of the lung at the acute angle relative to the pleural irregularity. In a sixth example of the method, optionally including one or more or each of the first through fifth examples, a user controls a position of the at least one virtual light source via a display of the 3D pleural surface. In a seventh example of the method, optionally including one or more or each of the first through sixth examples, the method further comprises: identifying and displaying B-lines for the 3D pleural surface.

The disclosure also provides support for a system, comprising: a display device, and a processor configured with instructions in non-transitory memory that, when executed, cause the processor to: generate a three-dimensional (3D) pleural surface viewed from an inside of a lung and looking outward, and output the 3D pleural surface for display on the display device. In a first example of the system, the system further comprises: an ultrasound probe configured to capture volumetric ultrasound data and/or two-dimensional (2D) ultrasound images. In a second example of the system, optionally including the first example, the processor is further configured with instructions in the non-transitory memory that, when executed, cause the processor to: construct a 3D mesh from a series of 2D images, and generate the 3D pleural surface from the 3D mesh. In a third example of the system, optionally including one or both of the first and second examples, the processor is further configured with instructions in the non-transitory memory that, when executed, cause the processor to: generate the 3D pleural surface by stacking a series of 2D images. In a fourth example of the system, optionally including one or more or each of the first through third examples, the system further comprises: a deep learning model trained for real-time and/or not real-time pleura detection in volumetric data. In a fifth example of the system, optionally including one or more or each of the first through fourth examples, the processor is further configured with instructions in the non-transitory memory that, when executed, cause the processor to: apply at least one virtual light source to the 3D pleural surface by positioning a virtual light source within the inside of the lung. In a sixth example of the system, optionally including one or more or each of the first through fifth examples, the system further comprises: a user interface communicably coupled to the processor and the display device, the user interface configured to receive inputs adjusting a position, a color, a brightness, and/or other characteristics of the virtual light source.

The disclosure also provides support for a method, comprising: acquiring volumetric ultrasound data, identifying a lung pleura in the volumetric ultrasound data, generating a three-dimensional (3D) pleural surface of the lung pleura viewed from an inside of a lung and looking outward based on the volumetric ultrasound data, removing volumetric ultrasound data on a side of the lung pleura towards the inside of the lung, applying a light source to the 3D pleural surface from the inside, and outputting the 3D pleural surface with the light source applied thereto for display. In a first example of the method, the 3D pleural surface is generated in real-time as ultrasound image data is acquired.

In a second example of the method, optionally including the first example, the 3D pleural surface is generated when ultrasound data acquisition is offline or frozen. In a third example of the method, optionally including one or both of the first and second examples, the method further comprises: selecting and outputting a representative 2D image of the 3D pleural surface, the representative 2D image including a pleural irregularity also shown in the 3D pleural surface. In a fourth example of the method, optionally including one or more or each of the first through third examples, applying the light source includes positioning a virtual light source in the inside of the lung at an angle relative to the 3D pleural surface.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A method for imaging a lung of a patient, comprising:
   generating an image of a three-dimensional (3D) pleural surface viewed from an inside of the lung and looking outward based on volumetric ultrasound data; and
   displaying the image of the 3D pleural surface, the image of the 3D pleural surface generated by:
   detecting a bottom edge of a pleura in the volumetric ultrasound data;
   removing ultrasound data from below the bottom edge of the pleura in the volumetric ultrasound data to create a new ultrasound dataset; and
   generating the image of the 3D pleural surface from the new ultrasound dataset.

2. The method of claim 1, wherein ultrasound imaging signals are captured by positioning a one-dimensional (1D), 1.5-dimensional (1.5D), or matrix (two-dimensional, 2D) probe.

3. The method of claim 1, wherein ultrasound imaging signals are captured by positioning a probe capable of live 3D imaging to acquire the volumetric ultrasound data.

4. The method of claim 1, wherein an outside of the patient is toward a top of the image and an inside of the lung is towards a bottom of the image.

5. The method of claim 1, further comprising shading the 3D pleural surface via at least one virtual light source positioned as if inside the lung at an acute angle relative to the 3D pleural surface.

6. The method of claim 5, wherein the shading comprises:
highlighting a pleural irregularity of the 3D pleural surface and positioning the at least one virtual light source within the inside of the lung at the acute angle relative to the pleural irregularity.

7. The method of claim 5, wherein a position of the at least one virtual light source is controlled via user input.

8. The method of claim 1, further comprising identifying and displaying B-lines for the 3D pleural surface.

9. A system, comprising:
a display device; and
a processor configured with instructions in non-transitory memory that, when executed, cause the processor to:
generate an image of a three-dimensional (3D) pleural surface viewed from an inside of a lung and looking outward, and output the image of the 3D pleural surface for display on the display device, wherein generating the image of the 3D pleural surface comprises:
detecting a bottom edge of a pleura in volumetric ultrasound data;
removing ultrasound data from below the bottom edge of the pleura in the volumetric ultrasound data to create a new ultrasound dataset; and generating the image of the 3D pleural surface from the new ultrasound dataset.

10. The system of claim 9, further comprising an ultrasound probe configured to capture volumetric ultrasound data and/or two-dimensional (2D) ultrasound images.

11. The system of claim 9, wherein the processor is further configured with instructions in the non-transitory memory that, when executed, cause the processor to:
construct a 3D mesh from a series of 2D images; and
generate the 3D pleural surface from the 3D mesh.

12. The system of claim 9, wherein the processor is further configured with instructions in the non-transitory memory that, when executed, cause the processor to:
generate the 3D pleural surface by stacking a series of 2D images.

13. The system of claim 9, further comprising a deep learning model trained for real-time and/or not real-time pleura detection in volumetric data.

14. The system of claim 9, wherein the processor is further configured with instructions in the non-transitory memory that, when executed, cause the processor to:
apply at least one virtual light source to the 3D pleural surface by positioning a virtual light source within the inside of the lung.

15. The system of claim 14, further comprising a user interface communicably coupled to the processor and the display device, the user interface configured to receive inputs adjusting a position, a color, a brightness, and/or other characteristics of the virtual light source.

16. The method of claim 1, further comprising selecting and outputting a representative 2D image of the 3D pleural surface, the representative 2D image including a pleural irregularity also shown in the 3D pleural surface.

\* \* \* \* \*